United States Patent [19]
Chance

[11] Patent Number: 5,987,351
[45] Date of Patent: Nov. 16, 1999

[54] OPTICAL COUPLER FOR IN VIVO EXAMINATION OF BIOLOGICAL TISSUE

[75] Inventor: Britton Chance, Marathon, Fla.

[73] Assignee: Non-Invasive Technology, Inc., Philadelphia, Pa.

[21] Appl. No.: 08/860,789

[22] Filed: Oct. 6, 1997

Related U.S. Application Data

[63] Continuation of application No. PCT/US96/00235, Jan. 2, 1996, which is a continuation-in-part of application No. 08/367,939, Jan. 3, 1995, Pat. No. 5,596,987.

[51] Int. Cl.$^6$ .......................................................... A61B 6/00
[52] U.S. Cl. ............................................ 600/473; 600/476
[58] Field of Search ..................................... 600/310, 322, 600/323, 326, 340, 344, 473, 476

[56] References Cited

U.S. PATENT DOCUMENTS

| | | | |
|---|---|---|---|
| 3,068,742 | 12/1962 | Hicks, Jr. et al. | ............................ 88/14 |
| 3,412,729 | 11/1968 | Smith, Jr. | ................................ 128/2.05 |
| 3,461,856 | 8/1969 | Polanyi | ........................................ 128/2 |

(List continued on next page.)

FOREIGN PATENT DOCUMENTS

| | | |
|---|---|---|
| 0 290 279 | 9/1988 | European Pat. Off. . |
| WO 92/20273 | 11/1992 | WIPO . |
| WO 94 16615 | 4/1994 | WIPO . |
| WO 96/20638 | 7/1996 | WIPO . |
| WO 97/20494 | 12/1997 | WIPO . |

OTHER PUBLICATIONS

Chance et al., "Photon Migration in Muscle and Brain," Photon Migration in Tissues, Plenum Press, pp. 121–135, 1989, Chance, B., ed.

Cui et al., "Experimental Study of Migration Depth for the Photons Measured at Sample Surface," *SPIE*, 1431:180–191, 1991.

Greenfeld, "A Tissue Model For Investigating Photon Migration in Trans–Cranial Infrared Imaging," *Photon Migration in Tissues*, Plenum Press, B. Chance, ed., pp. 147–168, 1989.

Sevick et al., "Analysis of absorption, scattering, and hemoglobin saturation using phase modulation spectroscopy," *SPIE*, 1431:264–275, 1991.

Sevick et al., "Photon migration in a model of the head measured using time–and frequency–domain techniques: potentials of spectroscopy and imaging," *SPIE*, 1431:84–96, 1991.

Weng et al., "Measurement of Biological Tissue Metabolism Using Phase Modulation Spectroscopy Technology," *SPIE*, 1431:161–171, 1991.

Primary Examiner—Cary O'Connor
Assistant Examiner—Eric F. Winakur
Attorney, Agent, or Firm—Fish & Richardson P.C.

[57] ABSTRACT

For in vivo examination using a spectrophotometer that generates optical radiation and characterizes biological tissue by detecting photons that have migrated in the tissue, an array of optical fibers that transmit radiation between the spectrophotometer and biological tissue, the fibers including distal ends freely protruding from a support in the manner of bristles from a hairbrush, forming an array of optical ports to couple photons to a contiguous tissue region or to collect photons from the tissue region, the optical fibers including proximal ends arranged to optically couple the radiation with the spectrophotometer. Also shown are: fibers sized and distributed to penetrate freely extending hair on the subject's head to make optical contact over an array of points with the scalp or skin; the array of fibers constructed as a handheld probe moved and placed against the head; optical matching material coupling between the fibers and the biological tissue region; and an irradiation array with the proximal fiber ends coupled to a light source, e.g. for brain tissue examination. Also shown are fibers as a detection array, e.g. for brain tissue examination or for imaging of the brain or for use in a magnet used for magnetic resonance imaging. The spectrophotometer is shown as a continuous wave spectrophotometer, phase modulation spectrophotometer, time resolved spectrophotometer and a phased array spectrophotometer.

20 Claims, 15 Drawing Sheets

U.S. PATENT DOCUMENTS

| | | | |
|---|---|---|---|
| 3,638,640 | 2/1972 | Shaw | 128/2 R |
| 3,709,612 | 1/1973 | Clemens | 356/178 |
| 3,866,599 | 2/1975 | Johnson | 128/2 L |
| 3,994,585 | 11/1976 | Frey | 356/40 |
| 3,998,550 | 12/1976 | Konishi et al. | 356/39 |
| 4,086,915 | 5/1978 | Kofsky et al. | 128/2 L |
| 4,119,406 | 10/1978 | Clemens | 422/81 |
| 4,138,727 | 2/1979 | Mantz | 364/525 |
| 4,162,405 | 7/1979 | Chance et al. | 250/461 |
| 4,167,331 | 9/1979 | Nielsen | 356/39 |
| 4,223,680 | 9/1980 | Jöbsis | 128/633 |
| 4,281,645 | 8/1981 | Jöbsis | 128/633 |
| 4,321,930 | 3/1982 | Jöbsis et al. | 128/633 |
| 4,380,240 | 4/1983 | Jöbsis et al. | 128/633 |
| 4,416,285 | 11/1983 | Shaw et al. | 128/634 |
| 4,510,938 | 4/1985 | Jöbsis et al. | 128/633 |
| 4,612,938 | 9/1986 | Dietrich et al. | 128/665 |
| 4,800,885 | 1/1989 | Johnson | 128/633 |
| 4,805,623 | 2/1989 | Jöbsis | 128/633 |
| 4,824,242 | 4/1989 | Frick et al. | 356/41 |
| 4,846,183 | 7/1989 | Martin | 128/633 |
| 4,908,762 | 3/1990 | Suzuki et al. | 364/413.09 |
| 4,972,331 | 11/1990 | Chance | 364/550 |
| 5,088,493 | 2/1992 | Giannini et al. . | |
| 5,090,415 | 2/1992 | Yamashita et al. | 128/665 |
| 5,106,387 | 4/1992 | Kittrell et al. | 606/15 |
| 5,119,815 | 6/1992 | Chance | 128/633 |
| 5,187,672 | 2/1993 | Chance et al. | 364/550 |
| 5,190,039 | 3/1993 | Takeuchi et al. | 128/633 |
| 5,300,097 | 4/1994 | Lerner et al. | 607/93 |
| 5,358,503 | 10/1994 | Bertwell et al. | 606/27 |
| 5,408,093 | 4/1995 | Ito et al. . | |
| 5,551,422 | 9/1996 | Simonsen et al. | 128/633 |
| 5,625,458 | 4/1997 | Alfano et al. . | |
| 5,655,530 | 8/1997 | Messerschmidt | 600/366 |
| 5,706,821 | 1/1998 | Matcher et al. | 600/310 |

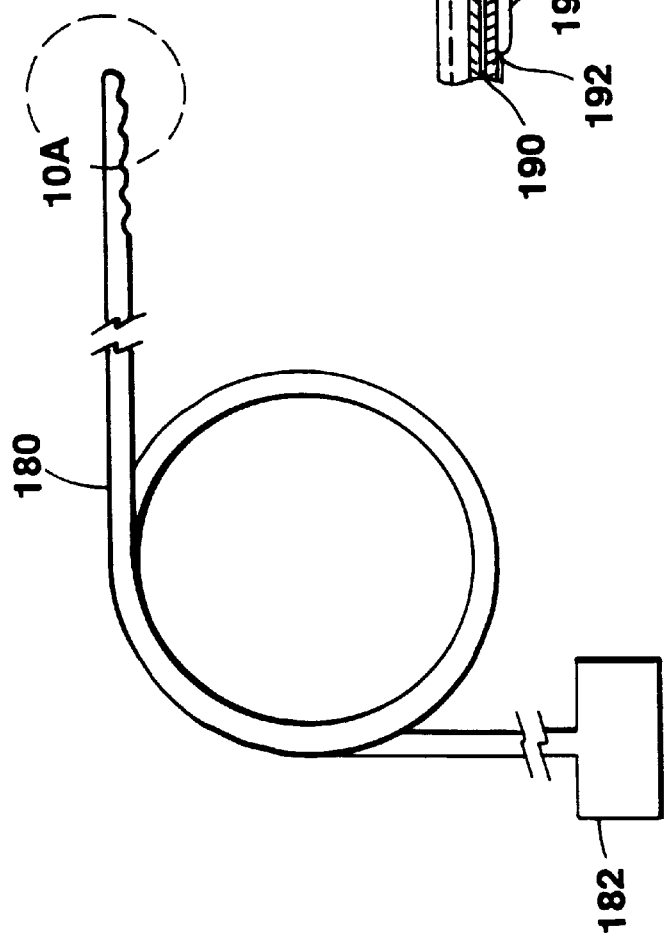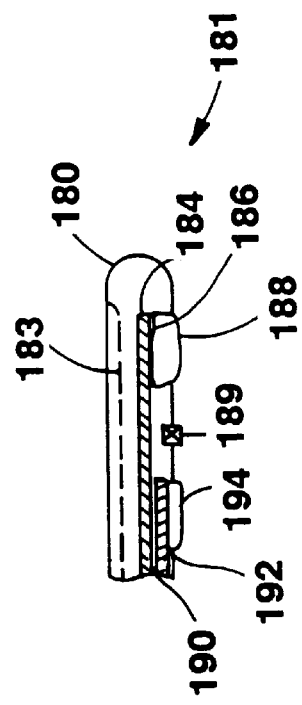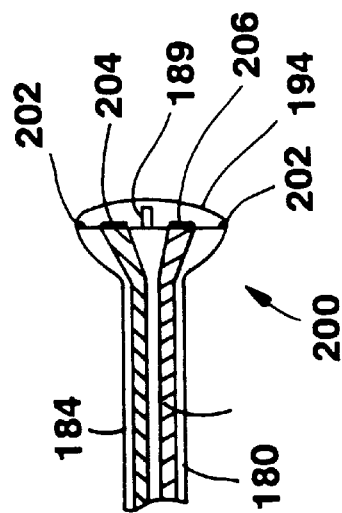

5,987,351

OPTICAL COUPLER FOR IN VIVO EXAMINATION OF BIOLOGICAL TISSUE

This is a continuation of pending International Patent Application No. PCT/US96/00235, with an international filing date of Jan. 2, 1996, which is a continuation-in-part of U.S. application Ser. No. 08/367,939 now U.S. Pat. No. 5,596,987, filed Jan. 3, 1995.

BACKGROUND OF THE INVENTION

Continuous wave (CW) spectrophotometers have been widely used to determine in vivo concentration of an optically absorbing pigment (e.g., hemoglobin, oxyhemoglobin) in biological tissue. The CW spectrophotometers, for example, in pulse oximetry introduce light into a finger or the ear lobe to measure the light attenuation and then evaluate the concentration based on the Beer Lambert equation or modified Beer Lambert absorbance equation. The Beer Lambert equation (1) describes the relationship between the concentration of an absorbent constituent (C), the extinction coefficient ($\epsilon$), the photon migration pathlength $<L>$, and the attenuated light intensity ($I/I_o$).

$$\frac{\log[I/I_0]}{\langle L \rangle} = \sum \epsilon_i C_i \quad (1)$$

However, direct application of the Beer Lambert equation poses several problems. Since the tissue structure and physiology vary significantly, the optical pathlength of migrating photons also varies significantly and can not be simply determined from geometrical position of a source and detector. In addition, the photon migration pathlength itself is a function of the relative concentration of absorbing constituents. As a result, the pathlength through an organ with high blood hemoglobin concentration, for example, will be different from the same with a low blood hemoglobin concentration. Furthermore, the pathlength is frequently dependent upon the wavelength of the light since the absorption coefficient of many tissue constituents is wavelength dependent. One solution to this problem is to determine $\epsilon$, C, and $<L>$ at the same time, but this is not possible with the pulse oximeters known previously.

Furthermore, for quantitative measurement of tissue of a small volume (e.g., a finger) photon escape introduces a significant error since the photons escaped from the tissue are counted as absorbed. Other errors may occur due to irregular coupling of light to the examined tissue or varying relative geometry of the input and detection ports.

The time resolved (TRS-pulse) and phase modulation (PMS) spectrophotometers can measure the average pathlength of migrating photons directly, but the proper quantitation of the time resolved or frequency resolved spectra can be performed only when the spectra are collected at a relatively large source-detector separation. This separation is difficult to achieve for a small volume of tissue such as the earlobe, a finger or a biopsy tissue.

Therefore, there is a need for a optical coupler used with a spectrophotometric system and method that quantitatively examines a relatively small volume of biological tissue.

SUMMARY OF THE INVENTION

The invention features a spectrophotometric system for examination of a relatively small volume of biological tissue of interest using visible or infra-red radiation.

According to one aspect of the invention, a spectrophotometric system for examination of a relatively small object of interest (e.g., biological tissue, organic or inorganic substance in a solid, liquid or gaseous state) using visible or infra-red radiation introduced to a path passing through the object. The system includes a spectrophotometer with an optical input port adapted to introduce radiation into the object and an optical detection port adapted to detect radiation that has migrated through a path in the object, photon escape preventing means arranged around the relatively small object of interest and adapted to limit escape of the introduced photons outside the object, and processing means adapted to determine an optical property of the object based on the changes between the introduced and the detected radiation.

According to another aspect of the invention, a system for examination of a relatively small volume of biological tissue of interest using visible or infra-red radiation includes a spectrophotometer with a light source adapted to introduce radiation at an optical input port, a detector adapted to detect radiation that has migrated through a path from the input port to an optical detection port, and a processor adapted to evaluate changes between the introduced and the detected radiation. The system also includes an optical medium of a relatively large volume, forming photon preventing means, having selectable scattering and absorptive properties, positioning means adapted to locate the biological tissue of interest into the migration path to create a tissue-medium optical path, the optical medium substantially limiting escape of photons from the tissue-medium optical path, and processing means adapted to determine a physiological property of the tissue based on the detected optical property of the tissue-medium optical path and the scattering or absorptive properties of the optical medium.

Preferred embodiments of these aspects of the invention include one or more of the following features.

The photon escape preventing means include an optical medium of a selectable optical property surrounding the object. The selectable optical property is an absorption or scattering coefficient.

The photon escape preventing means include an optical medium surrounding the object; the medium has at least one optical property substantially matched to the optical property of the object.

The spectrophotometer is a continuous wave spectrophotometer (CWS) as described in PCT applications WO 92/20273 and PCT/US95/15666, a phase modulation spectroscopic unit (PMS) as described in U.S. Pat. Nos. 4,972,331, 5,187,672, or a PCT application WO 94/21173, time resolved spectroscopic (TRS) unit as described in U.S. Pat. Nos. 5,119,815 or 5,386,827 or a PCT application WO 94/22361, or a phased array system as described in WO 93/25145, all of which are incorporated by reference as if set forth in their entireties herein.

The determined physiological property is the hemoglobin saturation, the concentration of an enzyme or the concentration of a tissue substance such as glucose.

The system performs a single measurement or a continuous, time-dependent monitoring of the selected physiological property.

The above-described system operates by introducing into the object, surrounded by the photon escape preventing means, electromagnetic radiation of a selected wavelength and detecting radiation that has migrated in the object from the input port to the optical detection port. The system determines an optical property of the object based on the changes between the introduced and the detected radiation. In addition, different photon escape preventing means having a surrounding optical medium with the optical property comparable to the optical property of the object may be selected. Then, the system measures again the optical property of the object. The measurements may be repeated iteratively until the optical property of the surrounding medium is substantially matched to the optical property of the object.

According to another important aspect, the invention is an optical coupling system for non-invasively monitoring a region of living tissue. The coupling system includes an excitation (input) port positionable at the tissue and adapted to introduce optical radiation into the monitored tissue, a first light guide defining an excitation channel for conveying the radiation from a source to the excitation port, and a detection port, positionable at the tissue, adapted to receive radiation that has migrated in the monitored tissue from the excitation port to the detection port. The detection port has a detection area larger than a input area of the excitation port. Connected to the detection port is a detecting light guide, for conveying the radiation from the detection port to an optical detector. The coupling system also includes optical matching fluid contained within a flexible optically transparent bag and disposed partially around the monitored tissue and the excitation and detection ports.

Preferred embodiments of this aspect of the invention includes one or more of the following features.

The optical coupling system may include multiple excitation (input) ports positionable at the tissue and adapted to introduce radiation of the source into the monitored tissue, and multiple light guides, each defining an excitation channel for conveying the radiation from the source to the corresponding excitation port.

The optical coupling system may also include multiple detection ports positionable at the tissue and adapted to receive radiation that has migrated in the monitored tissue, and multiple detecting light guides each connected to the corresponding detection port for conveying the radiation from the detection port to at least one optical detector.

The optical matching fluid may be positioned partially between the ports and the monitored tissue. The optical matching fluid may have known scattering or absorptive properties.

The optical coupling system may further include means for changing scattering or absorptive properties of the optical matching fluid and means for calibrating the coupling system by controllably changing scattering or absorptive properties of the optical matching fluid.

According to another important aspect, the invention is an optical coupler for in vivo examination of biological tissue. The optical coupler includes an optical input port of a selected input area positionable on or near the examined tissue, a first light guide optically coupled to the optical input port and constructed to transmit optical radiation of a visible or infra-red wavelength from a source to the optical input port, wherein the optical input port is constructed and arranged to introduce the optical radiation to the examined tissue, and an optical detection port of a selected detection area positionable on or near the examined tissue. The detection port is constructed and arranged to receive radiation that has migrated in the examined tissue from the input port to the detection port. Optically coupled to the detection port is a detector light guide constructed to transmit the radiation from the detection port to an optical detector. The optical coupler also includes optical medium disposed at least partially around the examined tissue and the input and detection ports and constructed to limit escape of, or account for photons escaped from the examined tissue.

According to another important aspect, the invention is an optical coupler for in vivo examination of biological tissue. The optical coupler includes an optical input port of a selected input area directed toward the examined tissue, an optical detection port of a selected detection area directed toward the examined tissue, and optical medium disposed at least partially around the examined tissue and the input and detection ports. The optical medium is also placed between the tissue and the input area of the input port and between the tissue and the detection area of the detection port, and the optical medium exhibits known scattering or absorptive properties. Optically coupled to the optical input port is a first light guide constructed to transmit optical radiation of a visible or infra-red wavelength from a source to the optical input port that is constructed and arranged to introduce the radiation to the optical medium. The optical detection port is constructed and arranged to receive radiation that has migrated in the examined tissue and the optical medium from the input port to the detection port. Optically coupled to the detection port is a detector light guide constructed to transmit the radiation from the detection port to an optical detector.

According to another important aspect, the invention is an optical coupling system for non-invasively monitoring a region of biological tissue. The coupling system includes a source probe made of at least two optical fibers having distal ends positionable directly at the tissue. Each distal end forms an input port constructed to introduce optical radiation into the examined tissue. The fibers have proximal ends constructed and arranged to form at least one coupling port for receiving the radiation from a source. The coupling system also includes a detection probe made of at least one optical fiber having a distal end positionable directly at the tissue. The distal end forms a detection port constructed to receive radiation that has migrated in the examined tissue. The fiber has a proximal end constructed and arranged to form at least one coupling port for conveying the detected radiation to an optical detector.

The optical fibers may include at the input port or at the detection port an optical matching medium arranged to achieve a desired coupling of the radiation.

Preferred embodiments of this aspect of the invention includes one or more of the following features.

The optical medium may have absorptive or scattering properties substantially matched to the absorptive or scattering properties of the examined tissue.

The optical coupler may further include an optical system constructed and arranged to alter controllably absorptive or scattering properties of the optical medium. The system may be adapted to substantially match the absorptive or scattering properties of the optical medium to the absorptive or scattering properties of the examined tissue.

The optical coupler may further include a second input port of a selected input area, and a light guide optically coupled to the second input port. The detection port may be placed symmetrically relative to the first input port and the second input port. The detection port may be arranged in a transmission geometry or in a backscattering geometry relative to the input ports.

The optical coupler may accommodate movable optical ports relative to the examined tissue.

The optical coupler may further include multiple input ports, and multiple light guides optically coupled to the corresponding input ports. The multiple input ports may be arranged to introduce simultaneously radiation of known time varying pattern to form resulting introduced radiation possessing a substantial gradient of photon density in at least one direction. The multiple input ports may form a one dimensional or two dimensional array. The optical detection port may be movable to another location relative to the examined tissue.

The optical coupler may also include multiple detection ports, and multiple detector light guides optically coupled to the corresponding detection ports.

The optical medium may be made of a solid, liquid, or gas. The optical medium may also include solid particles of smooth, spherical surface, or styrofoam. The optical medium may also include a liquid of selectable scattering or absorptive properties such as an intralipid solution. The optical medium may include a pliable solid of selectable scattering or absorptive properties.

The optical coupler may have the detection area of the optical detection port is larger than the input area of said optical input port.

The optical coupler may further include a port for the needle localization procedure or may be arranged for ultrasonic examination of the tissue performed simultaneously with, or subsequently to the optical examination of the tissue. The optical coupler may further include a set of MRI coils arranged to perform an MRI examination of the tissue.

The optical coupler may be disposed on an endoscope, catheter, guidewire or the like for insertion via a body passage, or transcutaneously, to internal tissue. The optical coupler is designed for visual and spectroscopic examination the selected internal tissue. The catheter may include an inflatable balloon that can press the input and detection ports against the tissue selected for spectroscopic examination. The catheter may also include a biopsy attachment for taking a biopsy specimen from a tissue region before or after the spectroscopic examination.

According to another important aspect, the invention is an optical coupler for in vivo examination of biological tissue. The optical coupler includes an optical input port of a first selected area directed toward the examined tissue and a second selected area oppositely oriented to the first area, and an optical detection port of a selected detection area directed toward the examined tissue. The input port is constructed to accept a light beam scanned over the second area and introduce the beam to the tissue at the first area. The optical coupler also includes optical medium disposed at least partially around the examined tissue and the input and detection ports. The optical medium is also placed between the tissue and the input area of the input port and between the tissue and the detection area of the detection port. The optical medium exhibits known scattering or absorptive properties. The optical detection port is constructed and arranged to receive radiation that has migrated in the examined tissue and the optical medium from the input port to the detection port. Optically coupled to the detection port is a detector light guide constructed to transmit the radiation from the detection port to an optical detector.

Preferred embodiments of this aspect of the invention includes one or more of the following features.

The detection area of the optical detection port may include a multiplicity of detection subareas located at a known position of the detection area. Each detection subarea is constructed and arranged to receive radiation that has migrated in the examined tissue and convey the received radiation to a detector.

The optical detector may include an array of semiconducting detectors each receiving light from a corresponding detection subarea via the detector light guide. Thus a time profile of the detected radiation can be measured at the individual locations.

The light beam may be scanned over the input port using a selected pattern relative to a detection sequence accumulated over the detection subareas. Then, by knowing the input and detection locations of the migrating photons, average photon migration paths may be calculated.

In general, the optical coupling system provides an excellent coupling of light to the examined tissue. The coupling system may also substantially prevent escape of photons from the tissue surface and achieve semi-infinite boundary conditions for the introduced radiation. A larger volume of optical medium is usually used for a small tissue size. The optical coupling system also achieves precisely a selected geometry of the input (excitation) ports and the detection ports regardless of the tissue shape or property. The precise geometry is frequently important for proper evaluation of the photon migration patterns measured by the continuous wave (CWS) unit, the phase modulation unit, the TRS unit, or the phased array unit.

BRIEF DESCRIPTION OF THE DRAWING

FIGS. 10, 10A and 10B depict an optical coupler disposed on a catheter.

DESCRIPTION OF THE PREFERRED EMBODIMENTS

Figure 1:
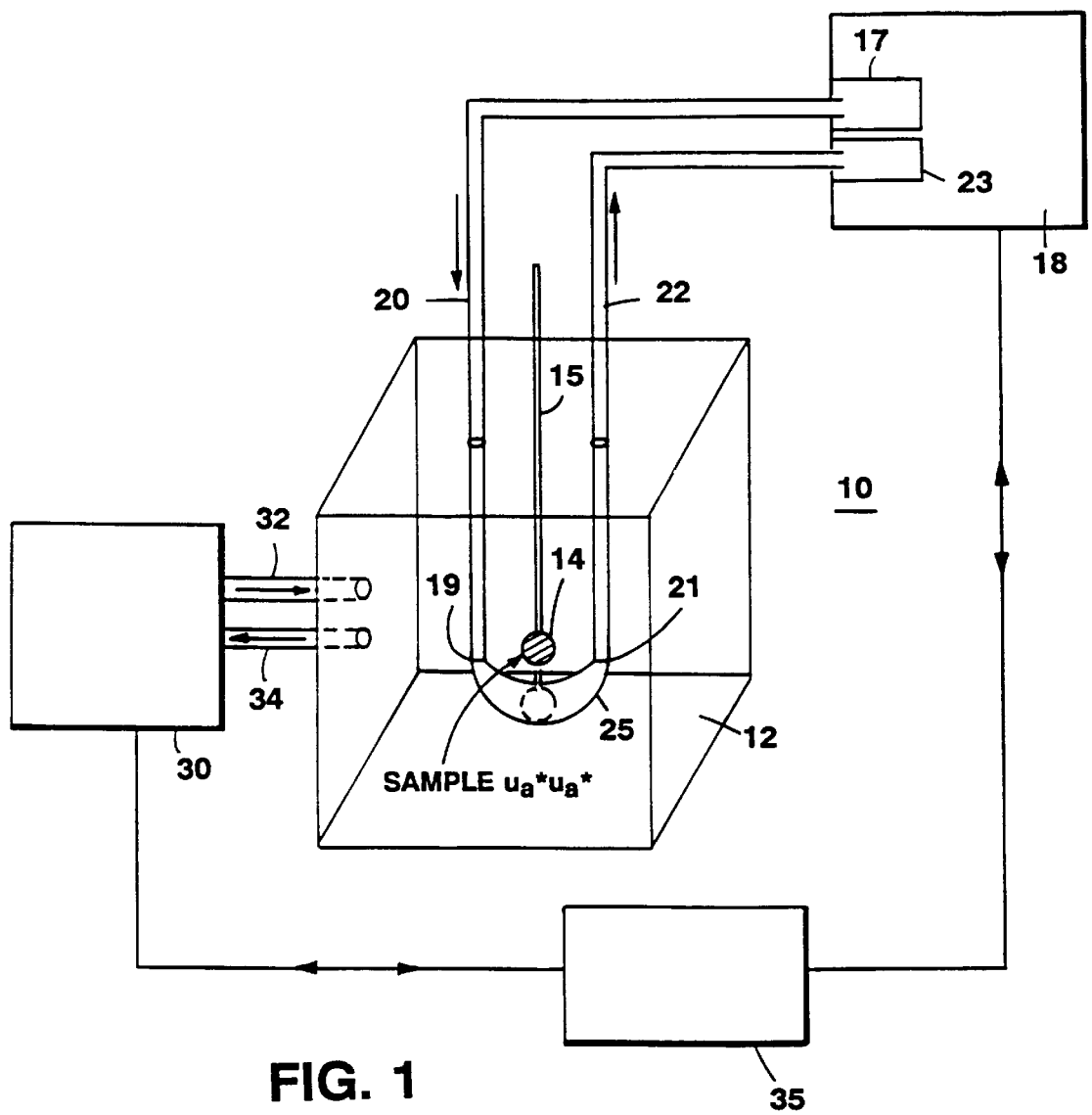
FIG. 1 is a diagrammatic view of a spectrophotometric system for examination of tissue of a relatively small dimension.

Referring to FIG. 1, the basic principle of operation of different optical couplers is explained by describing a system 10. System 10, designed for examination of biological tissue of a relatively small volume, includes an optical medium 12 of selectable optical properties, a spectrophotometer 18, a titrimetric circulation system 30, and computer control 35. Biological tissue of interest 14, attached to a locator 15, is immersed in optical medium 12. Spectrophotometer 18 examines optical properties of medium 12 by employing visible or infra-red light conducted via light guides 20 and 22. Light guides 20 and 22, which in a preferred embodiment are optical fibers, are connected to a light source 21 and a light detector 23, respectively. Photons introduced at an optical input port 19 migrate in medium 12 through a scattering and absorptive path and are detected at a detection port 21. The selectable fixed geometry of input port 19 and detection port 21 controls the migration path, i.e., optical field 25.

System 30 is adapted to change precisely the scattering and absorptive properties of medium 12. Medium 12 includes intralipid solution (made by Kabi Vitrum, Inc., Clapton, N.C.) that exhibits scattering properties depending on its concentration and carbon black india ink that exhibits absorptive properties. The scattering or absorptive properties of medium 12 can be either maintained constant and uniform by properly mixing the solution or can be changed almost continuously by changing the concentration of the constituents in titration system 30. Tubes 32 and 34 are adapted for continuous circulation of the solution.

In system operation, tissue 14 is first located away from optical field 25. Spectrophotometer 18 examines medium 12 in field region 25, and control 35 compares the detected data to the preselected values of the absorption coefficient ($\mu_a$) and the scattering coefficient ($\mu_s$). Next, locator 15 positions tissue 14 into field 25 and spectrophotometer 18 measures the optical properties of tissue 14 and medium 12. From the spectral data collected with and without tissue 14, computer control 35 determines the optical properties of tissue 14.

In another preferred method of operation, after measuring the optical properties of medium 12, the scattering and absorptive properties of medium 12 are matched by titration to the properties of tissue 14 so that, when inserted into field 25, tissue 14 does not cause perturbation of field 25. After matching the scattering and absorption coefficients of medium 12 to the coefficients of tissue 14, spectrophotometer 18 detects the same data with or without tissue 14. The known titrated values of $\mu_a^*$ and $\mu_s^*$ are equal to the $\mu_a$ and $\mu_s$ values of tissue 14. The matching process is performed by first matching $\mu_a$ and then $\mu_s$ or vice versa.

The described method is applicable to both in vivo and in vitro tissue examination. Tissue 14 may be a biopsy specimen enclosed in an optically transparent material or a portion of a human finger inserted into medium 12. The wavelength of light used by spectrophotometer 18 is selected depending on the tissue component of interest (e.g., hemoglobin, oxyhemoglobin, glucose, enzymes); it is within the scope of this invention to use multiple wavelengths.

Figure 2:
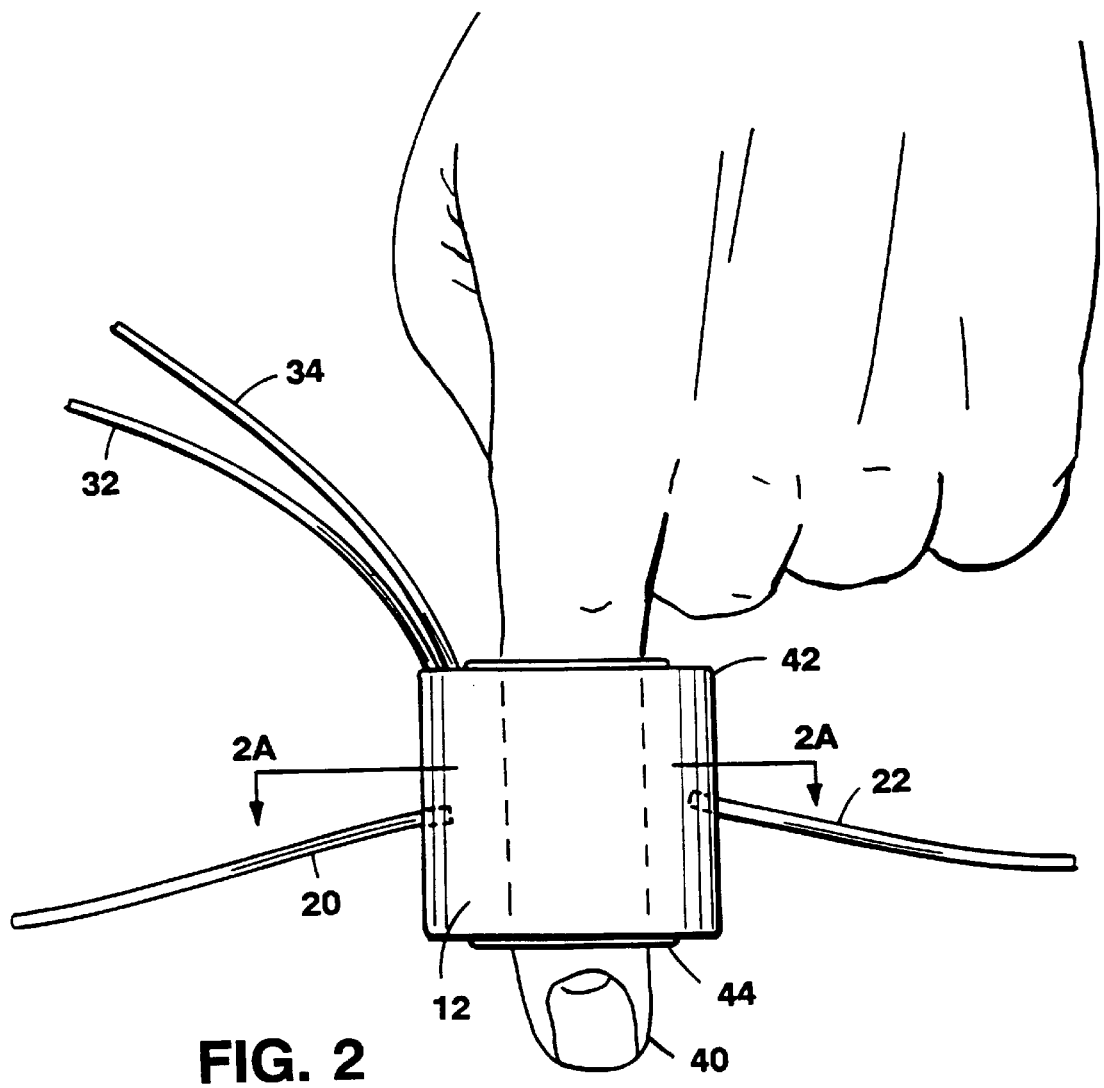
FIGS. 2 and 2A show different views of a cylinder for preventing escape of photons during spectrophotometric measurements of a finger.

The present invention envisions the use of different preferred embodiments of optical medium 12. Referring to FIG. 2, a hollow cylinder 42 filled with medium 12 surrounds, for example, a finger 40 and prevents escape of introduced photons. The optical properties, pressure and volume of medium 12 are controlled by system 30 connected to cylinder 42 by tubes 32 and 34. The inside walls of cylinder 42 are made of a pliable, optically transparent barrier 44. After insertion into cylinder 42, barrier 44 fits snugly around the finger. The dimension of inside barrier 44 is such that after finger 40 is withdrawn, medium 12 fills the volume of cylinder 42 completely. This enables both a background measurement of medium 12 and a measurement of finger 40 in medium 12 in the same way as described in connection with FIG. 1. Optical field 25, controlled by the position of input port 19 and detection port 21, is either in transmission or reflection geometry.

Figure 2A:
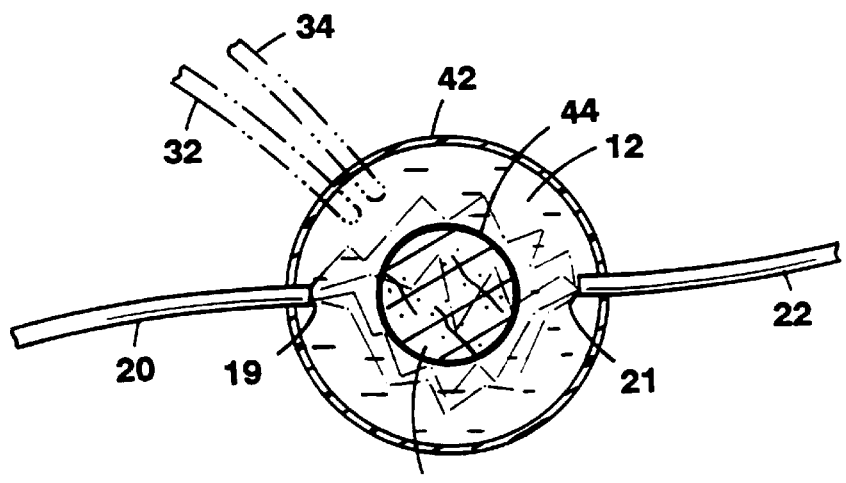
Figure 2B:
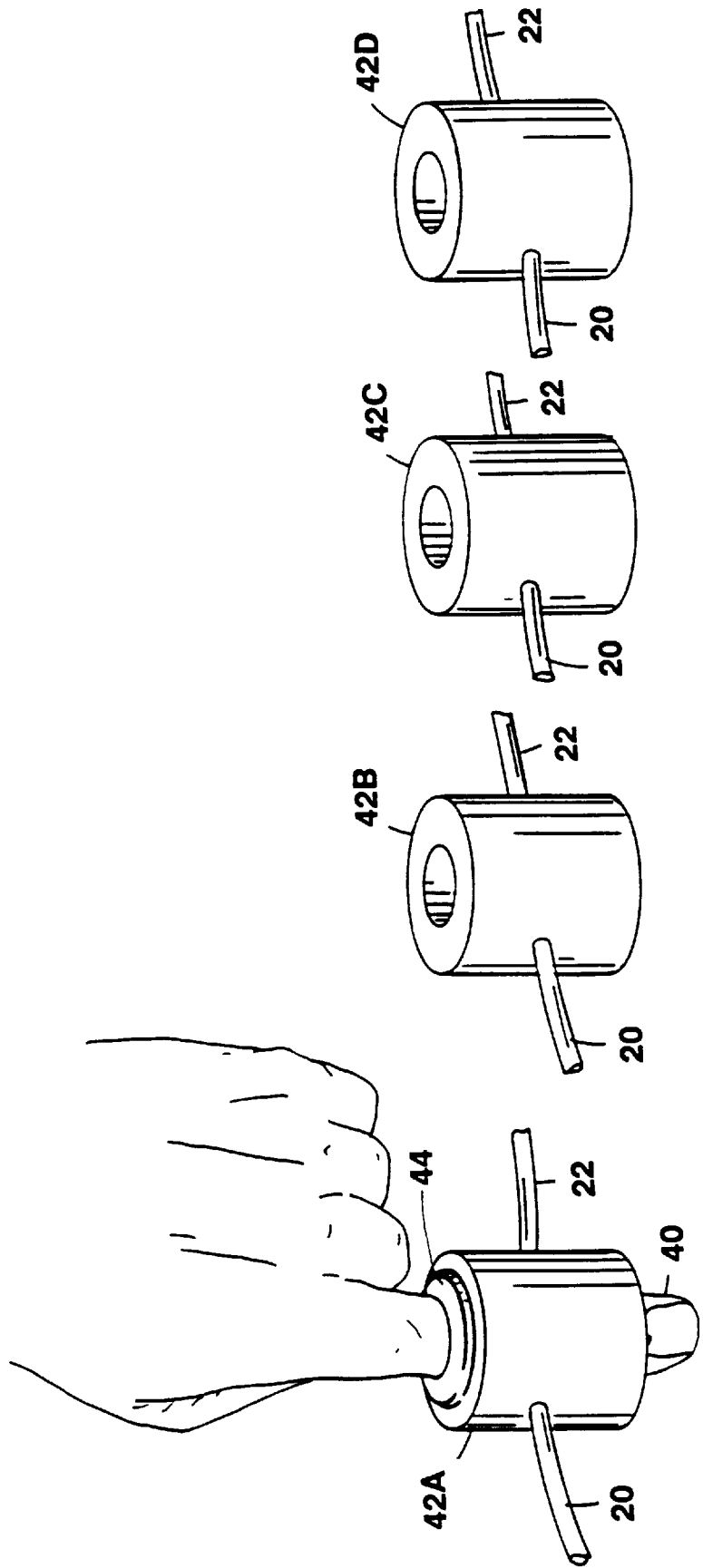
FIG. 2B shows a set of cylinders of preselected optical properties for a finger oximetry.

Referring to FIG. 2B, in another embodiment, cylinder 42 is replaced by a set of cylinders 42A, 42B, 42C . . . , each containing medium 12 in a fluid or solid state with a constant preselected absorption and scattering coefficient. The solid optical medium is titanium oxide, or other scatterer, imbedded in an absorbing, pliable medium such as a gel.

A human finger is inserted into the individual cylinders, and the optical properties of the inserted finger are measured by spectrophotometer 18. Using the known optical properties of the cylinders and the input port-detection port geometry, the optical properties (i.e., $\mu_a$ and $\mu_s$) of the finger can be matched to the properties of one of the cylinders.

The preferred embodiments of spectrophotometer 18 are a continuous wave spectrometer, a phase modulation spectrometer and a time-resolved spectrometer, all of them described in the above-cited documents.

System 10 operating with a dual wavelength continuous wave spectrometer is used, for example, as a finger oximeter. As shown in FIG. 2A, the vast majority of photons introduced into finger 40 are prevented to escape by surrounding medium 12. Thus, the introduced photons are either absorbed or reach detection port 21 and are registered by the detector. No error of counting the escaped photons as absorbed occurs. The background spectral data corresponding to each selected value of $\mu_a^*$ and $\mu_s^*$ of cylinder 42 are stored in the system that can match the values of $\mu_a$ and $\mu_s$ of the finger and the cylinder for each wavelength. For the continuous wave spectrometer that operates at two wavelengths sensitive to hemoglobin (Hb) and oxyhemoglobin (HbO$_2$) (e.g., 754 nm and 816 nm), the hemoglobin saturation (Y) is calculated by taking the ratio of absorption coefficients and using the following equation for the oxygen saturation:

$$Y(X\ 100\%) = \frac{38 - 18\dfrac{\mu_a^{754}}{\mu_a^{816}}}{25 + 3\dfrac{\mu_a^{754}}{\mu_a^{816}}} \qquad (2)$$

wherein the coefficients are determined from the extinction values of hemoglobin at 754 nm and 816 nm that are $\epsilon_{HB}$=0.38 cm$^{-1}$ mM$^{-1}$, $\epsilon_{Hb}$=0.18 cm$^{-1}$ mM$^{-1}$, respectively, and the difference extinction coefficients between oxyhemoglobin and hemoglobin that are $\Delta\epsilon_{HbO-Hb}$=0.025 cm$^{-1}$ mM$^{-1}$ and $\Delta\epsilon_{HbO-Hb}$=0.03 cm$^{-1}$ mM$^{-1}$, respectively.

As known to a person skilled in the art, in the hemoglobin saturation measurement the oximeter normalizes the detected data to eliminate fluctuations due to the changing blood volume. However, the volume changes can be used to detect the pulse rate.

Alternatively, a phase modulation spectrometer is used to measure the photon migration by detecting the intensity and the phase shift θ of sinusoidally modulated light introduced at a distance of several centimeters from the detector. For tissue of a small volume, the optimal distance between the input port and the irradiation port is achieved using optical medium 12. Furthermore, medium 12 substantially eliminates the photon escape.

The detected phase shift is directly related to the mean of the distribution of photon pathlengths shown in FIG. 2A.

Photon migration theory predicts that the detected photons can be represented by a three dimensional "banana-shaped" distribution pattern in the reflection geometry or a "cigar-shaped" distribution pattern in the transmission geometry. Inserting tissue 14 into the center of field 25 causes non-uniformities in the distribution of pathlengths, i.e., the banana-shaped optical field 25 is nonuniform, if the tissue absorption properties are different from the properties of medium 12. If $\mu_a$ of the tissue is smaller then that of the surrounding medium, the average pathlength <L> decreases since photons with longer pathlengths are more absorbed and vice versa. Thus, tissue 14 causes changes in the pathlength and the phase shift, θ.

Furthermore, the detected intensity provides a modulation index (M) that is an important measure of the absorption and scattering properties of a strongly scattering medium. The modulation index is determined as the ratio of the AC amplitude ($A^\lambda$) to the sum of the AC and DC ($DC^\lambda$) amplitude.

$$M^{\lambda_1} = \frac{A^{\lambda_1}}{A^{\lambda_1} + DC^{\lambda_1}} \tag{3}$$

As described in Sevick et al. in Analytical Biochemistry Vol. 195, pp. 330–351, 1991, incorporated by reference as if set forth herein, for low modulation frequencies (i.e., $2\pi f \ll \mu_a c$) the phase shift is a direct measure of the mean time of flight, <t>, i.e., $\theta \rightarrow 2\pi f <t>$. In a medium wherein all photons travel at a constant speed, c, the phase shift describes the effective, mean pathlength $\theta \rightarrow 2\pi f <L>/c$. Here, all pathlengths are weighted equally. The determined pathlength is used in Beer-Lambert equation for determination of the absorption properties.

As the modulation frequency increases, the shorter pathlengths become more heavily weighted. At frequencies (i.e. $2\pi f \gg \mu_a c$), the phase shift is no longer a good measure of the distribution of pathlengths and is directly proportional to the absorption coefficient, $\mu_a$, and the effective scattering coefficient, $(1-g)\cdot\mu_s$.

$$|\theta^\lambda| = a\rho\sqrt{(1-g)\mu_s f}\left\{1 - \frac{\mu_a C}{4\pi f}\right\} \tag{4}$$

Since the effective scattering coefficient is wavelength independent, ratio of the phase shifts measured at two wavelengths can be written $$\frac{\theta^{\lambda_1} - \theta_0^{\lambda_1}}{\theta^{\lambda_2} - \theta_0^{\lambda_2}} = \frac{\mu_a^{\lambda_1}}{\mu_a^{\lambda_2}} \tag{5}$$

wherein $\theta_o^\lambda$ is the phase shift at the measured wavelength arising from the scattering and background absorption. The ratio of the absorption coefficients is used, for example, for determination of the tissue saturation, Y. A dual frequency, dual wavelength phase modulation spectrometer can be used to determine the saturation by eliminating $\theta_o$. The ratio of absorption coefficients is expressed as a function of the phase shifts measured at different frequencies and wavelengths.

$$\frac{(\theta_{f_1}^{\lambda_1}/\sqrt{f_1}) - (\theta_{f_2}^{\lambda_1}/\sqrt{f_2})}{(\theta_{f_1}^{\lambda_2}/\sqrt{f_1}) - (\theta_{f_2}^{\lambda_2}/\sqrt{f_2})} = \frac{\mu_s^{\lambda_1}}{\mu_s^{\lambda_2}} \tag{6}$$

Alternatively, a time-resolved spectrometer (TRS-pulse) is employed which introduces, at input port 19, pulses of light on the order of less than a picosecond. Photons traveling through a distribution of migration pathlengths 25 are collected at the detection port 21. The intensity of detected light in the reflectance geometry, R(ρ,t), (or the transmittance geometry T(ρ,d,t)) was determined by solving the diffusion equation in an infinite media as a Green's function with near infinite boundary conditions. Due to the semi-infinite media condition in the reflectance geometry, the separation of the input and output ports must be on the order of several centimeters to use the following equation.

$$\frac{d}{dt}\log_e R(\rho,t) = \frac{-5}{2t} - \mu_a C + \frac{\rho^2}{4DCt} \tag{7}$$

For t→∞ the absorption coefficient $\mu_a$ is determined as $$\lim_{t\to\infty}\frac{d}{dt}\log_e R(\rho,t) = -\mu_a c \tag{8}$$

wherein ρ is the separation between input and detection ports and c is speed of light in the medium. The effective scattering coefficient $(1-g)\mu_s$ is determined as $$(1-g)\mu_s = \frac{1}{\rho^2}(4\mu_a c^2 t_{max}^2 + 10ct_{max}) - \mu_a \tag{9}$$

wherein $t_{max}$ is the delay time at which the detected reflectance time profile $(R(\rho,t)\equiv I(t))$ reaches maximum. The right hand side of Eq. 7 is the decay slope of the arrival time of the modified pulses. The absorption coefficient is quantified by evaluating the decaying slope of the detected pulse, as described in Eq. 7. The effective scattering coefficient, $(1-g)\cdot\mu_s$, is determined from Eq. 9. For the known $\mu_a$ and $\mu_s$ and the input port, output port geometry, the system has a unique time profile I(t). The stored profile is compared to the time profile detected for the introduced tissue to obtain a difference profile that possesses the scattering and absorption coefficients of tissue 14. Alternatively, $\mu_a$ and $\mu_s$ of medium 12 and tissue 14 are matched by varying the scattering and absorptive properties of medium 12 so that the detected time profile is not altered by introducing tissue 14.

The TRS system can be used to calibrate a CW oximeter to quantify the measured data. To account for the difference between the geometric distance (ρ) of the input port and the detection port and the pathlength (<L>), some oximeters use a modified Beer-Lambert equation with a differential pathlength factor (DPF) as follows:

$$\text{absorbance} = DPF \cdot \epsilon \cdot [C] \tag{10}$$

However, the differential pathlength factor can not be precisely determined by the CW oximeters since it depends on the pathlength. The TRS determines DPF using the absorption ($\mu_a$) and scattering ($\mu_s$) coefficients as follows:

$$DPF = \frac{\sqrt{3}}{2} \sqrt{\frac{(1-g)\mu_s}{\mu_a}} \quad (11)$$

Alternatively, a phased array spectrometer, described in WO 93/25145, is employed to localize a tissue anomaly or image a selected tissue region.

The described systems are constructed to perform either a single measurement or a continuous, time-dependent monitoring of the selected physiological property. The may include a visual display for continuous monitoring of the measured values and may include a alarm that issues a warning signal when the measured value equals to a preselected value.

Figure 3:
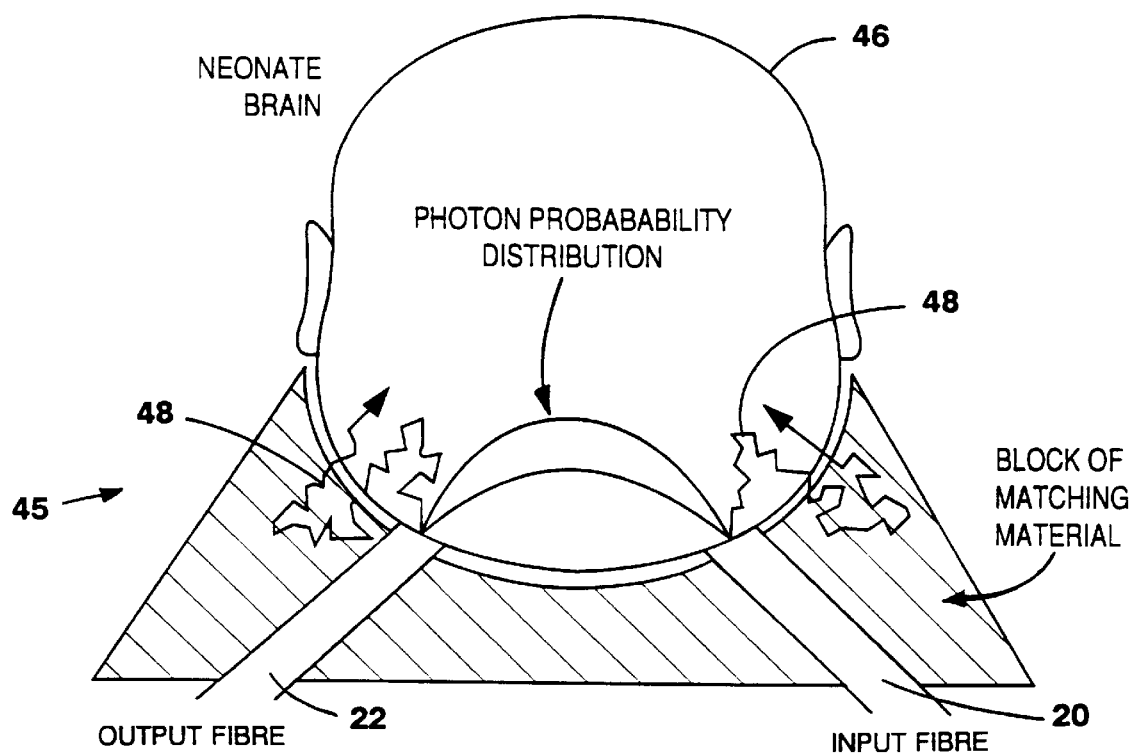
FIG. 3 is a diagrammatic view of an optical fiber holder for a spectrophotometric study of the head.

An alternative embodiment of the optical coupler is an optrode holder 45 shown in FIG. 3. Optrode holder 45 is used for examination of the head of a neonate (46). Optical fibers 20 and 22 are projected into a solid scattering material 47, i.e., an escape preventing optical medium, such as styrofoam, which affords a return pathway for escaping photons 48. The pathlength of the migrating photons in the tissue is much longer since the photons return to the tissue by the scattering materials, as shown by the zig-zag arrows 48. Thus, the banana-shaped pattern will penetrate more deeply and meaningful spectroscopic data can be obtained at smaller input-output fiber separations without the danger of photon leakage or "short" by substantially direct pathways. Alternatively, the styrofoam may be replaced by a metallic foil that reflects back to the tissue radiation of visible or near infrared wavelengths. The foil surrounds the input and detection ports and the examined tissue.

Figure 4:
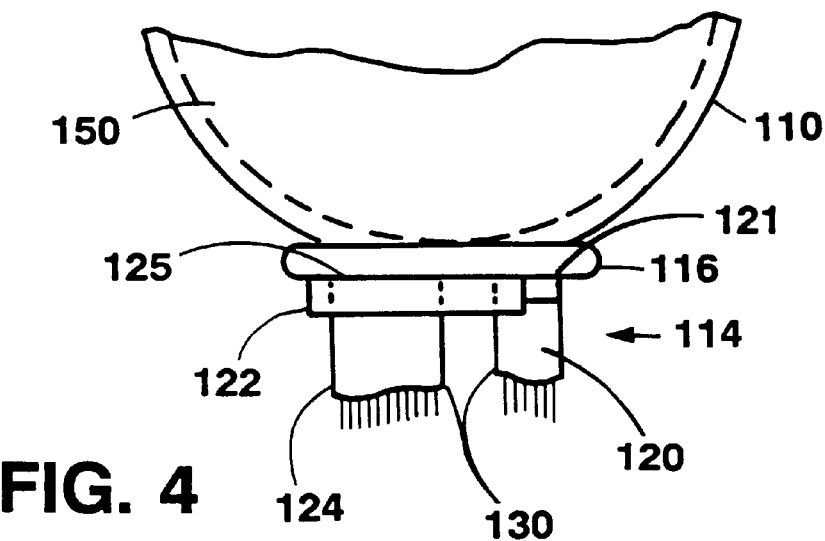
FIG. 4 a plan view of an optical coupling system for monitoring the oxygenation-deoxygenation state of the hemoglobin within the brain tissue of a subject.

Referring to FIG. 4, another embodiment is an optical coupling system that comprises an optical coupling device 114 and a spacer-coupler 116 for coupling the forward end of optical coupling device 114 to the back of the head 110 to monitor a tissue region of the brain. (A similar system can monitor other tissue regions, such as internal organs and muscles.) The spacer-coupler 116 is a thin, flexible, liquid-filled bag that is inflated by optical matching fluids to the condition depicted. The spacer-coupler 116 also serves as a cushion, providing a soft interface between the forward end of the coupling device 114 and the head 110.

The optical coupling device 114 comprises a light guide 120 in the form of a bundle of optical fibers constituting an excitation channel for supplying near red radiation (NR) from the rear of the coupling device to head 110. The distal end 121 of the light guide 120 adjacent the head 110 forms an excitation port. A detecting light guide 124, which is also comprised of optical fibers, extends along the length of the coupling device. Surrounding a distal end 125 of detecting light guide 124 is an opaque specular barrier 122. The barrier blocks substantially all direct and reflected radiation except that migrating from a region spaced from the tissue surface; i.e., barrier 122 acts as an absorber of the near-surface rays. This enables the connected spectrophotometer to determine, for example, the oxygenation state of hemoglobin deep within the tissue rather than at the surface. To block the leakage of the radiation from the length of the excitation light guide into the detecting light guide, a thin coating 130 of material substantially opaque to the radiation is preferably placed around each of the fiber optic bundles 120, 124.

The monitoring systems of FIG. 4 can be calibrated by the flowing of a mixture of yeast cells and blood of known oxygenation properties through the spacer-coupler 116 to determine the ab initio sensitivity of the system to oxy-deoxy-hemoglobin solutions of blood. The accuracy of the monitoring system can be improved by compensating for changes of the albedo of the hair and skin of the subject and also for changes in the thickness of the spacer-coupler 116. Such compensation can be achieved by providing an annulus of optical fibers closely surrounding the excitation light guide 120, but separated therefrom by an opaque coating. The excitation radiation supplied through the light guide 120 and detected by the annulus of fibers at the forward end of the coupling device can be used to monitor the backscattered radiation and also regulate the lamp intensity so as to maintain constant incident radiation.

Figure 4A:
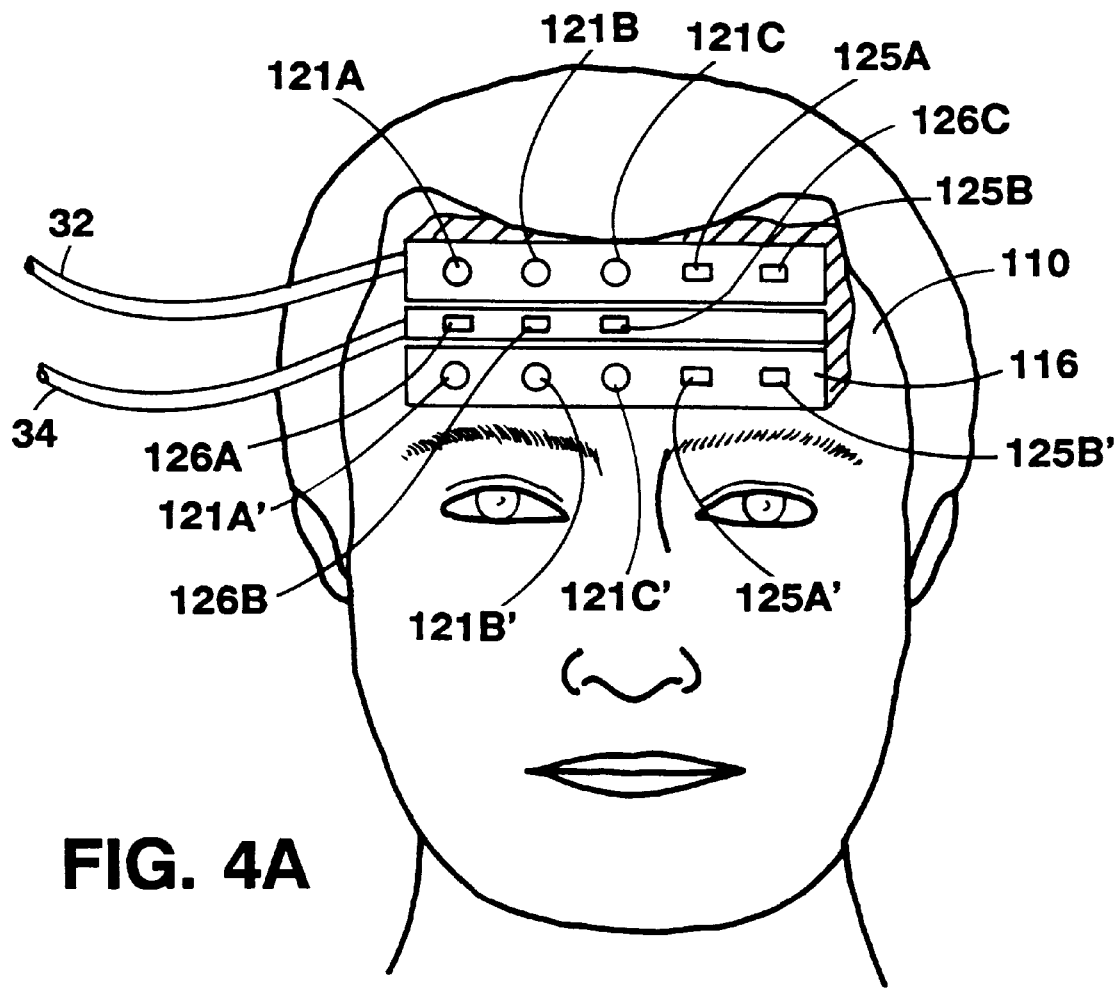
FIG. 4A depicts an optical coupling system for examination of the brain tissue utilizing several input and detection ports.

A similar coupling system is shown in FIG. 4A. The coupling system includes a spacer-coupler 116 and two sets of excitation ports 121A, 121B, 121C, and detection ports 125A and 125B, each arranged in a row, and a central row of detection ports 126A, 126B and 126C. The input area of the excitation ports has a diameter of 100 $\mu$m to 1 mm and the detection area of the detection ports has a diameter of 1 mm to 10 mm. The larger detection area is used to increase the collection of the migrating photons. As described above, tubes 32 and 34 are connected to a titration system and used for circulation and controlled optical changes of the optical matching fluid contained within a pliable, optically transparent barrier. As described above, the scattering or absorption properties ($\mu_a$, $\mu_s'$) of the optical medium may be selected to match $\mu_a$ of the tissue, $\mu_s'$ of the tissue or both. In several applications, it is advantageous to match $\mu_s'$ and keep $\mu_a$ very low to substantially eliminate absorption in the optical medium. Thus the absorption coefficient will mainly depend on the properties of the examined tissue.

Each row of the excitation ports and the detection ports may be used for independent examination of the brain tissue by performing a $\rho$-scan as described in a PCT/US 95/15666, incorporated by reference as if set forth herein. Light guides deliver radiation to individual excitation ports 121A, 121B, 121C in sequence and the introduced photons migrate through the patient's brain to detection ports 125A, 125B over the corresponding, "banana-shaped" migration paths that depend on the excitation port—detection port separation. Based on the detected, normalized intensities, the spectrophotometer calculates the values of $\mu_a$ and $\mu_s'$ that are used to detect a brain bleed, a cerebral hypoxia or tissue plaque characteristic of Alzheimer's disease.

The central row of detection ports 126A, 126B and 126C is used for a separate phased array measurement described is a PCT/US 95/15694, incorporated by reference as if set forth herein. Light from two sources is introduced into the examined brain tissue at excitation ports 121A and 121A', sequentially. The intensities of the two sources are selected so that a detection port 126A is located on a null plane of equal intensity in the tissue. A detector detects sequentially radiation that has migrated from the input ports 121A and 121A' to detection port 126A. The detected signals are stored in a sample-and-hold circuit and subtracted in a subtraction circuit to create a differential signal. The differential signal is then used to examine the tissue. This cancellation measurement is performed over the three sets of excitation and detection ports (i.e., 121A, 121A', and 126A; 121B, 121B', and 126B; 121C, 121C', and 126C, respectively) to examine the frontal lobe of the brain.

Figure 5:
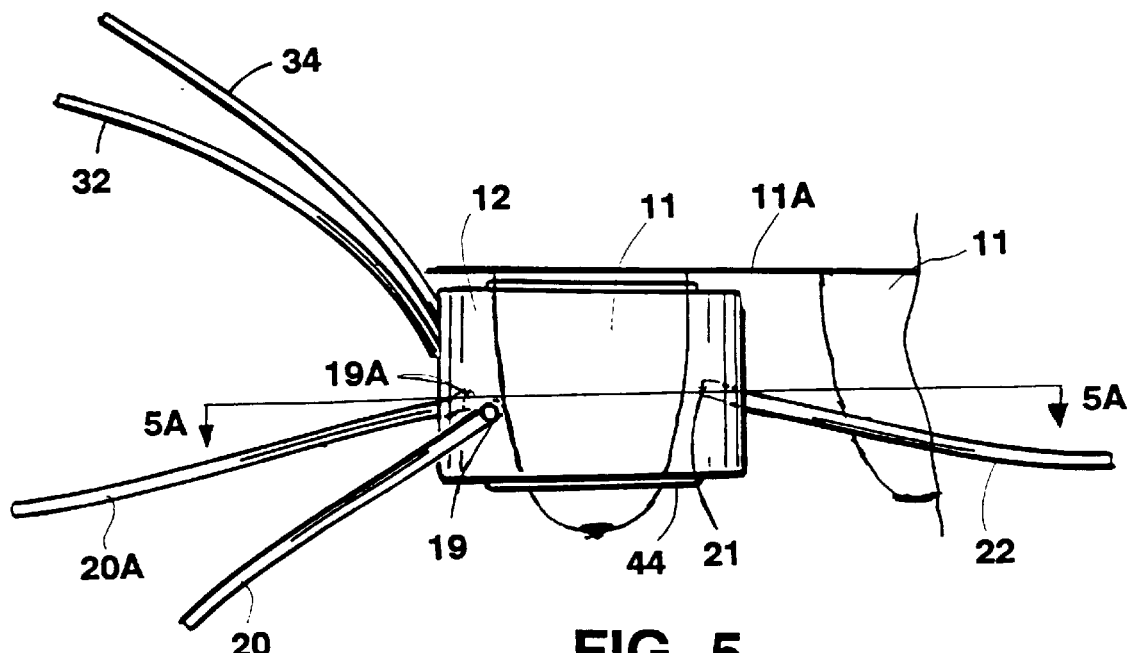
FIGS. 5 through 5C depict several optical coupling systems for optical examination of the breast tissue.

Referring to FIG. 5, similar type of the optical coupling system is used to examine breast tissue 11. A cylindrical optical coupler includes a hollow cylinder 42 filled with optical medium 12. Cylinder 42 is placed over the breast 11 near the chest wall 11A. As described above, the optical properties, pressure and volume of medium 12 are controlled by system 30 connected to cylinder 42 by tubes 32 and 34. The optical matching fluid is contained within pliable, optically transparent barrier 44. The inside walls of cylinder 42 may be coated with a film that reflects light in the visible or near infra-red range back to the matching fluid. The optical coupler uses cylinders 42 of different sizes or a cylinder with an adjustable volume so that the coupler can have a selected distance between the breast surface and the inside wall of cylinder 42. The preferred distance is about 1 centimeter, but for a very small tissue a larger distance is preferable to achieve semi-infinite boundary conditions. Thus the coupler is also useful for examination of the breast of a small size or after a surgical removal of the breast tissue. After placement of cylinder 42, the volume of medium 12 is adjusted so that barrier 44 fits snugly around the examined breast. Alternatively, the optical medium is a pliable solid, for example, an absorbing gel containing metallic or oxide spherical particles, or silky glass beads as scatterers. When the cylinder is placed firmly on the examined breast, the excess optical medium contained within the pliable barrier is pushed outside of the cylinder.

As described above, spectrophotometer 18 measures the optical properties of tissue 11 and medium 12. Light guides 20 and 20A are connected to light source 21, and light guide 22 is connected to light detector 23. Photons introduced at an optical input ports 19 and 19A migrate in medium 12 over scattering and absorptive paths and are detected at detection port 21. The optical medium achieves a uniform coupling of light to the tissue that is usually pliable and enables preselected fixed geometry of the input end detection ports. Spectrophotometer 18, which is a continuous wave spectrophotometer, a phase modulation spectrophotometer or time resolved spectrophotometer, evaluates the breast tissue similarly as described above for the biopsy specimen or the finger.

Furthermore, the optical resolution may be increased when spectrophotometer 18 together with the optical coupler are calibrated on a "normal" tissue region and then used to examine another tissue region that when "normal" should have the same optical properties as the first tissue region. For example, the optical coupler is first placed on the left breast and the optical properties of the tissue are measured. Then, the optical coupler is placed on the right breast suspected to have an abnormal tissue region. The optical properties of the right breast are measured and evaluated relative to the optical properties of the normal tissue of the left breast. The relative measurement can be performed by measuring the two sets of data independently and subtracting or comparing them to them to each other. Alternatively, two spectrophotometers, each with an optical coupler placed on one breast, are used simultaneously using a lateralization detector. Such technique is described in general (and specifically for examination the brain) in a PCT application WO 92/20273, filed May 18, 1992, incorporated by reference as if set forth herein.

Figure 5A:
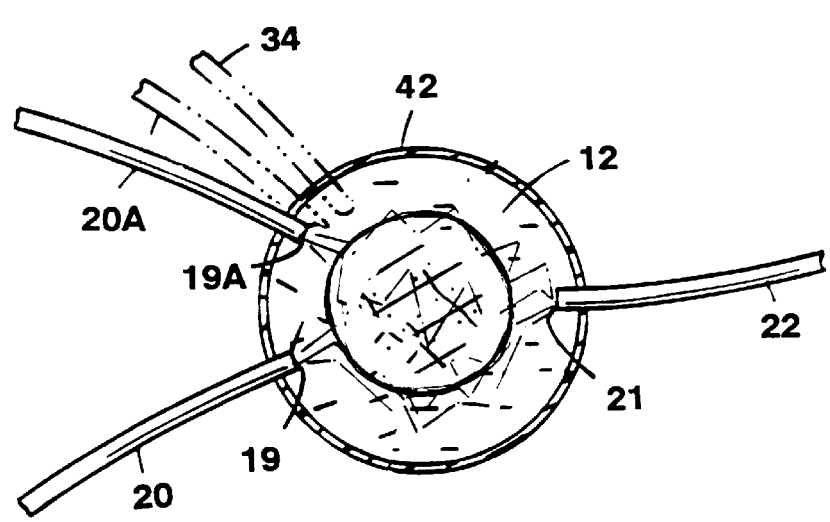
FIG. 5D depicts an optical coupling system with a two dimensional input array also adapted for the needle localization procedure.
FIGS. 5E and 5F depict optical coupling systems adapted for optical examination together with ultrasound and magnetic resonance imaging, respectively.
Figure 5B:
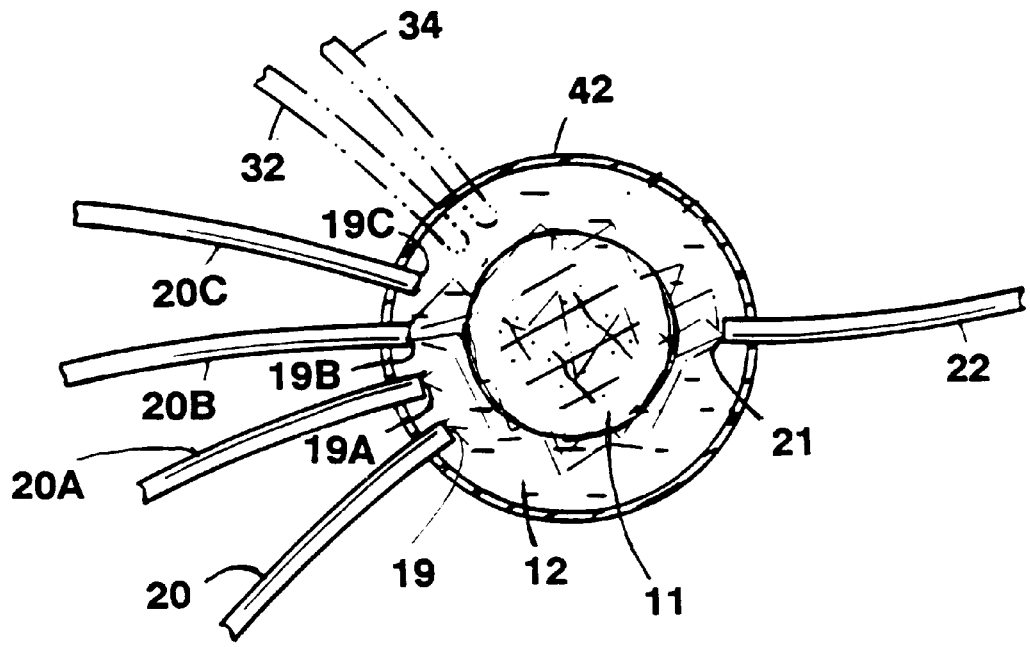
Figure 5C:
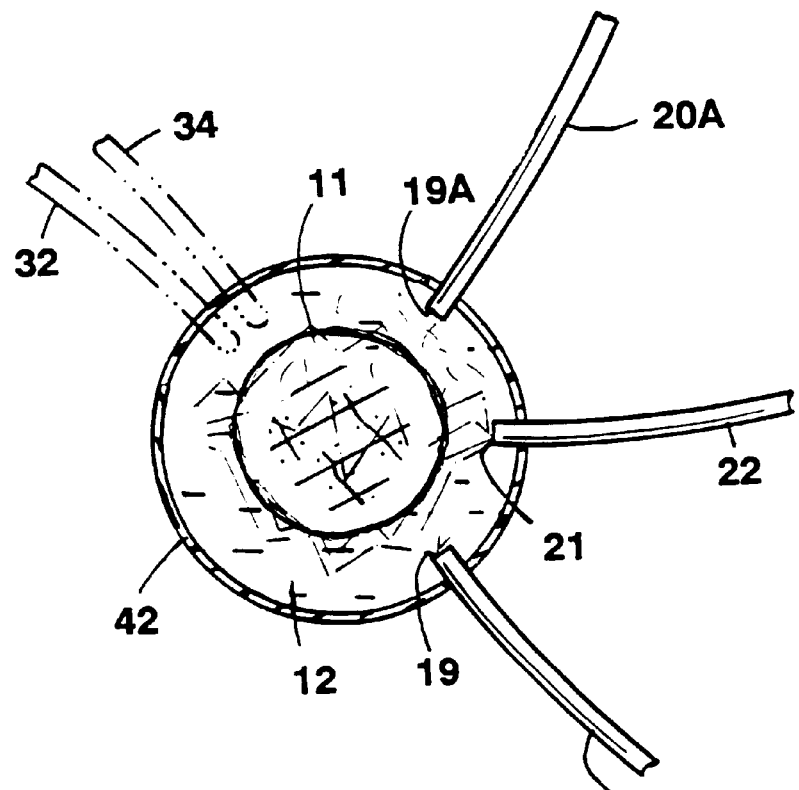

Alternatively, spectrophotometer 18 is a phased array system described in the PCT/US 95/15694 application cited above. FIG. 5A depicts an optical coupler for a measurement using a transmission geometry, and FIG. 5B depicts an optical coupler for a measurement using a reflection geometry that was already described for coupling system of FIG. 4A. FIG. 5C depicts an optical coupler for a phased array system that introduce simultaneously from input ports 19, 19A, 19B and 19C radiation of known time varying pattern that form resulting introduced radiation possessing a substantial gradient of photon density in at least one direction. The directional introduced radiation is perturbed by a tissue inhomogeneity (e.g., a tumor, bleeding) and is detected at the detection location 21. Cylinder 42 may include a slit opening to accommodate movement of fiber 22 so that detection port 21 may be located at several different positions. The tissue is examined or imaged by scanning the introduced directional field in two or three dimensions and moving the detection port over a predetermined geometry, as described in the WO 93/25145 document.

Figure 5D:
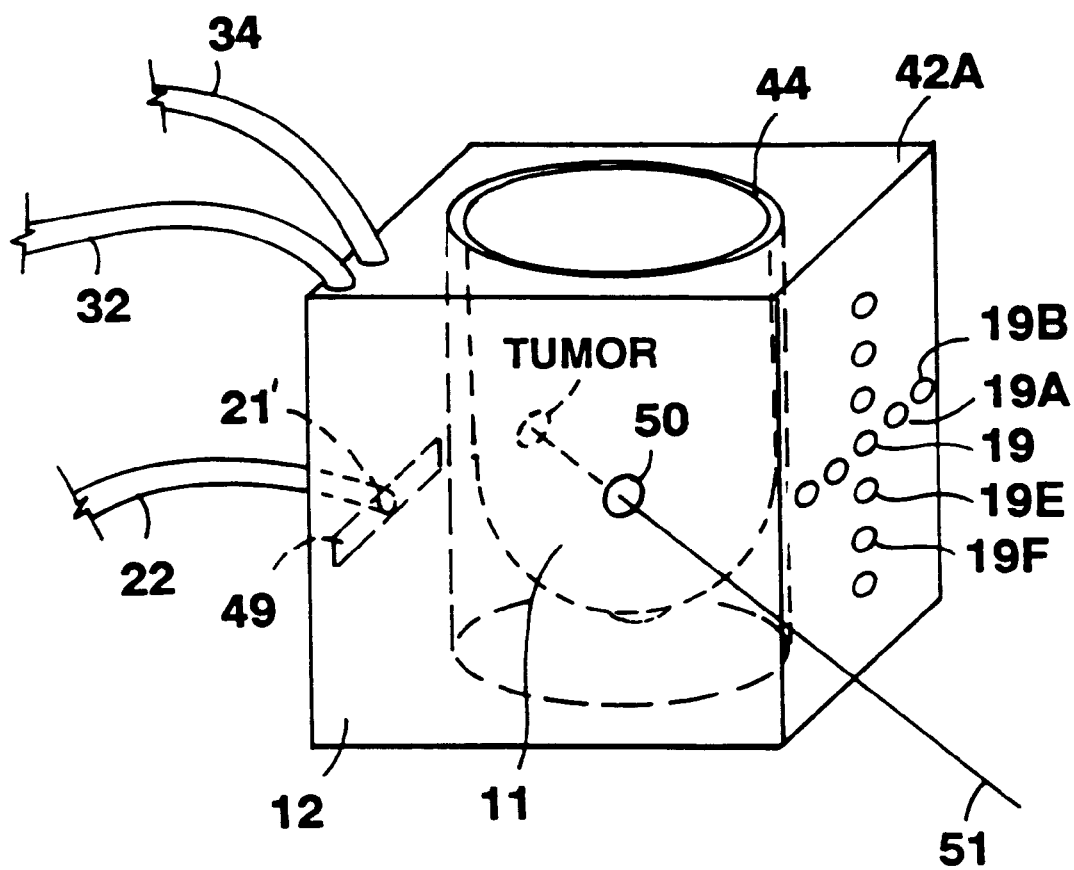

A similar optical coupler for a two dimensional phased array system is shown in FIG. 5D. A hollow box 42A filled with optical medium 12 contained within a pliable, optically transparent barrier 44 includes several optical input ports 19, 19A, 19B, 19C, . . . , arranged to form a two dimensional array, and a slit 49 constructed to receive detection port 21 of detection fiber 22 or an optical window. Alternatively, port 19 can be used as the detection port in a backscattering geometry. The coupler may also include a port 50 adapted for the needle localization procedure. (If another access is needed, port 19 may be constructed to accommodate both an optical fiber or the needle.) The inner walls of box 42A are lined with a reflecting material that returns photons back to fluid 44. When the coupler is used in the needle localization procedure, the tumor is first identified by X-ray pictures taken through box 42A. While the X-ray pictures are taken, optical fluid 44 may be withdrawn to avoid high attenuation of X-rays. Then, needle 51 is placed through port 50 to mark the tumor with a metal wire. The tumor is then examined or localized using the two dimensional phased array. Ports 19 or 50 may also be used for biopsy of the localized tumor.

Figure 5E:
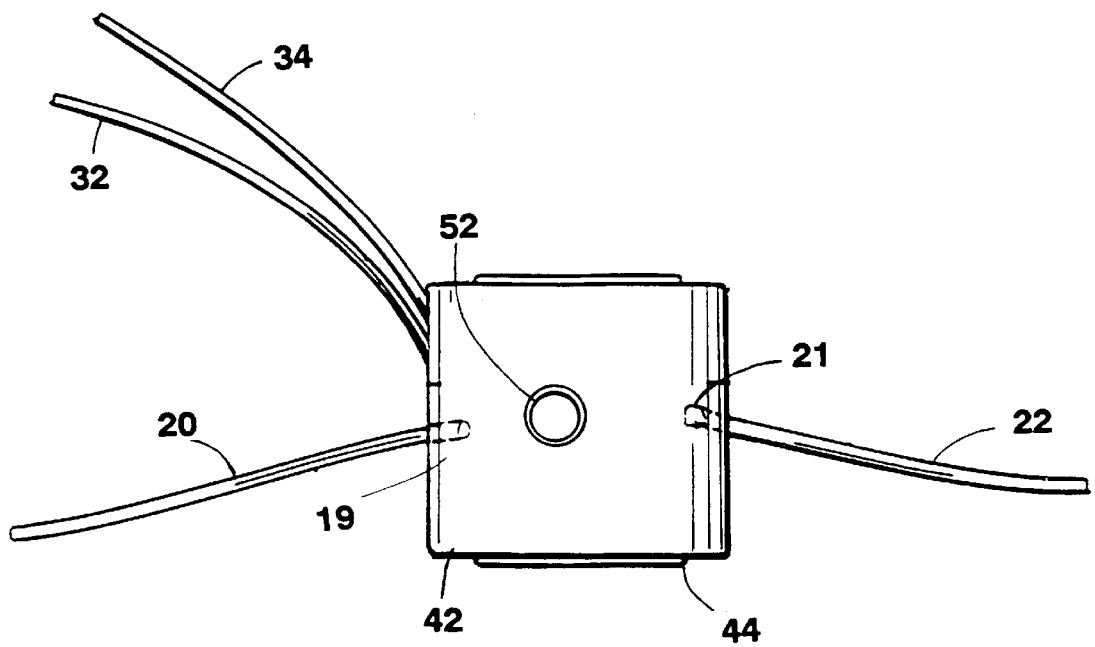
Figure 5F:
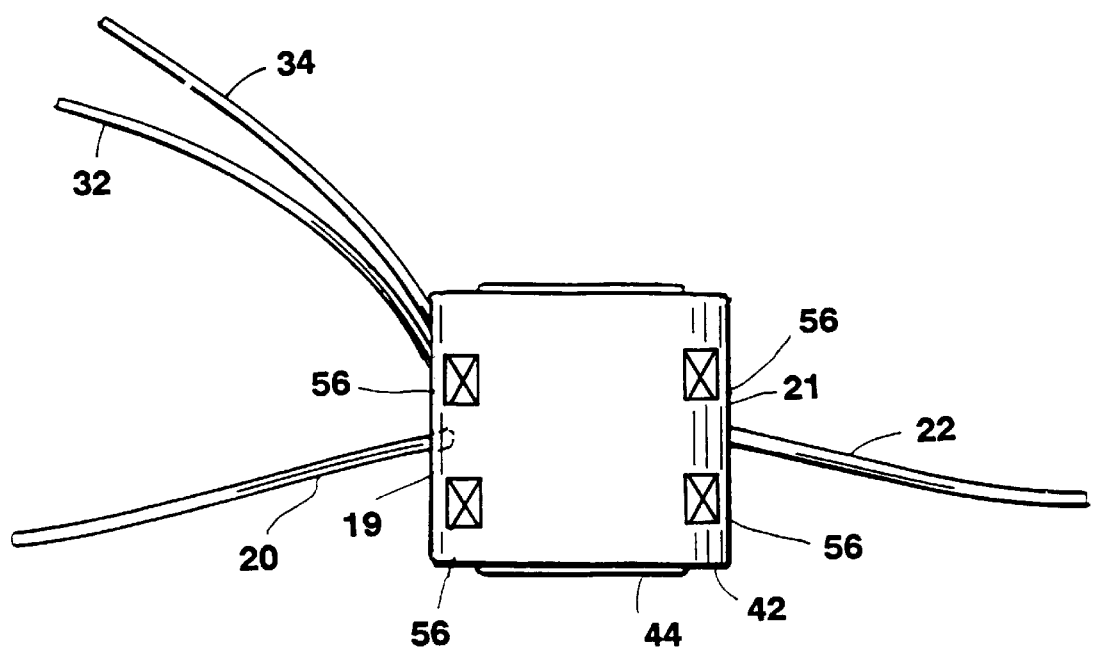

Optical couplers used for ultrasound examination and magnetic resonance imaging in conjunction with the optical spectroscopy are depicted in FIGS. 5E and 5F, respectively. Referring to FIG. 5E, the optical coupler of FIG. 5 includes a port 52 constructed to accept an ultrasound probe. Referring to FIG. 5F, the optical coupler for magnetic resonance imaging is made of non-magnetic materials and includes a set of MRI coils 56 located around the tissue. The tissue is imaged by using both MRI and optical techniques, wherein the image resolution may be increased using contrast agents suitable for both MRI and optical examination, as described in the WO 94/22361 application, incorporated by reference as if set forth herein.

Figure 6:
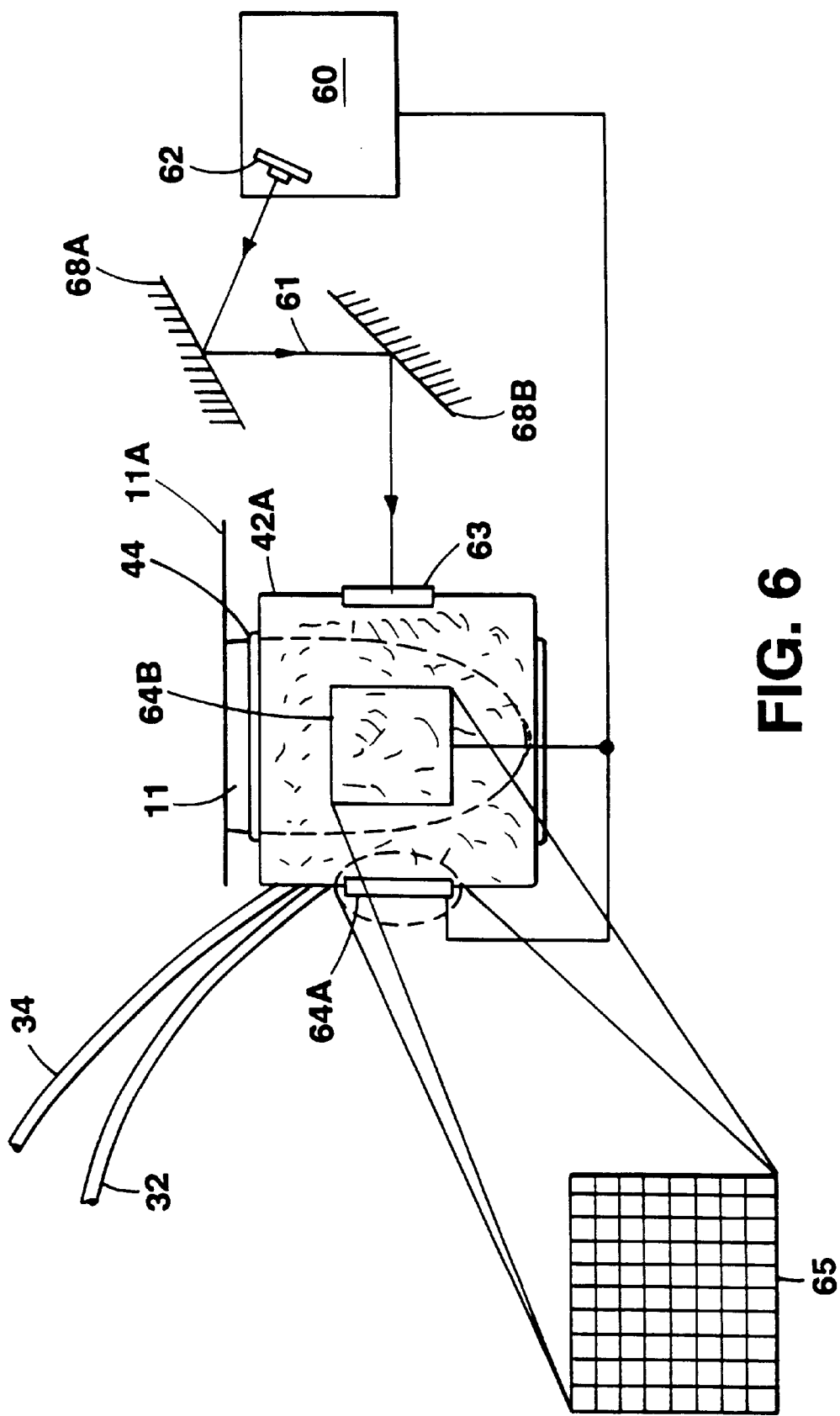
FIG. 6 depicts an optical coupling system with optical windows adapted for a scanning system with an array detector.

Referring to FIG. 6, in another embodiment, the optical coupler includes a set of optical windows instead of the input and detection fibers. The coupler includes a hollow cylinder 42A, filled with optical medium 12 contained within a pliable barrier, which has three optical windows 63, 64A and 64B. A light beam emitted from a light source 62 of a spectrophotometer 60, is directed to a selected location of input port 63 by a set of mirrors 68A and 68B and other optical elements. The optical system stores the exact position of the input beam relative to the examined tissue. After migration in tissue 11, the altered light is detected at detection ports 64A or 64B using a detector 65. Detector 65 includes, for example, an array of semiconducting detectors. Optical detection ports 64A or 64B are formed from an array of detection subareas, and each subarea conveys received radiation to the corresponding semiconducting detector. Thus, the system can record intensity and exact co-ordinates of the detected radiation. Based on the known input radiation and its co-ordinates and detected radiation for the individual detector locations, the system characterizes the tissue as described in the PCT application WO 93/25145.

Figure 7A:
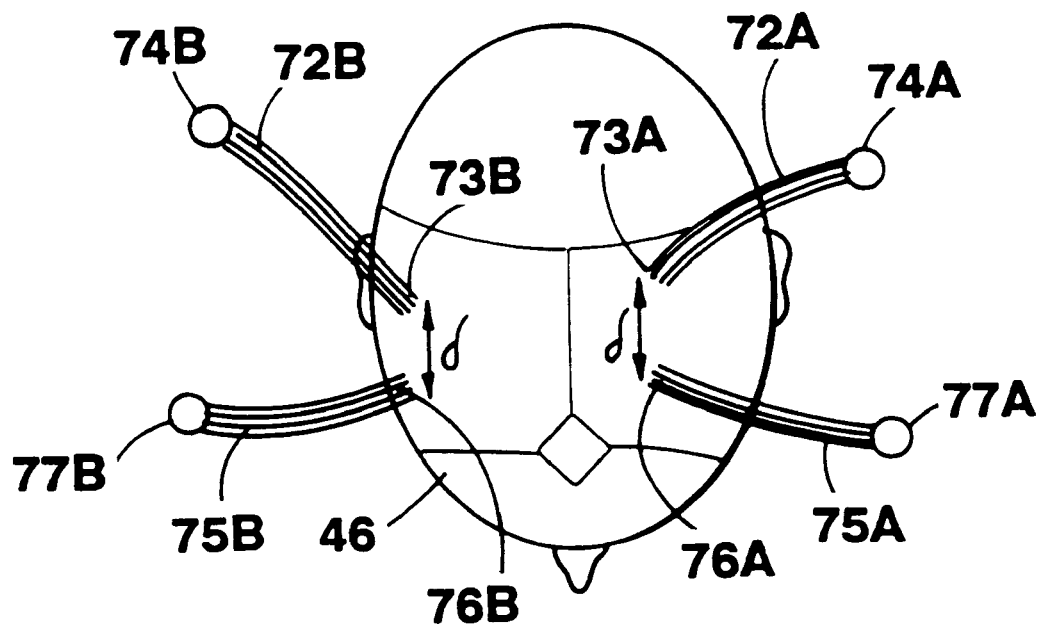
FIGS. 7 and 7A depict a "hairbrush" optical coupling system for optical examination of the brain.
Figure 7:
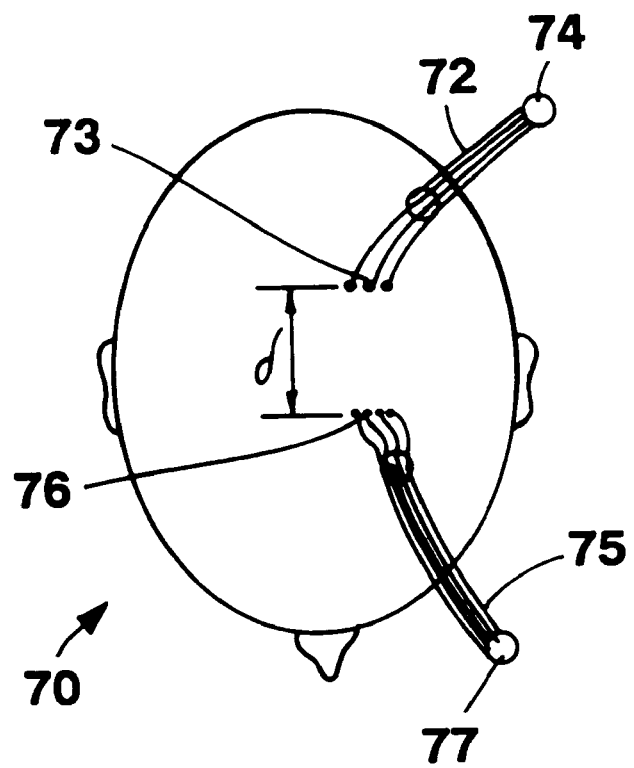

Referring to FIG. 7, another embodiment of the optical coupling system is a hairbrush optical coupler 70. This optical coupler is designed to provide optimal coupling of light to and from brain tissue in regions where the skull is covered by hair. Coupler 70 includes at least one source probe 72 and at least one detection probe 75. Source probe 72 is made of approximately twenty optical fibers of 0.5 millimeter to 3 millimeter in diameter and at least one half centimeter in length. Input ports 73 (i.e., irradiation tips) of the fibers of source probe 72 are arranged to form a selected structure (e.g., a matrix, mosaic, circular or linear structure) depending on the desired input geometry and the type of the examined tissue. Each irradiation tip of the fiber may include an optical matching material (e.g., a plastic, a gel-like material, a coating or the like) located between the fiber and the tissue and designed to introduce light efficiently into the examined tissue. At the proximal end, probe 72 has one or more light coupling ports 74. The probe has a single light coupling port made of the fibers bundled together and arranged to achieve efficient coupling of light from a light source (e.g., a light bulb, a light emitting diode, a laser) to the probe. Alternatively, the probe has multiple light coupling ports (e.g., one port per fiber), wherein the generated light is coupled into the fibers sequentially or simultaneously.

Detection probe 75 includes one or more detection ports 76 and one or more light coupling ports 77. Detection probe 75 has a similar design as source probe 72, but may have a larger number of individual fibers in order to collect a sufficient amount of light that has migrated in the tissue. At the proximal end, the detection fibers may also be bundled together to form a single light coupling port 77, which provides good coupling to a wide area detector (e.g., a diode detector, a PMT detector or a MCPD detector). Since source probe 72 and detection probe 75 have a similar construction, they may be used interchangeably. Several source probes and detection probes may be coupled to an optical sequencer or multiplexer constructed to transmit and receive light in a desired manner. The probes are made of cladded fibers to eliminate crosstalk.

Source probe 72 and detection probe 75 are mounted on a support member constructed to achieve a selected position of the fibers and a desired separation of the input ports and the detection ports. The support member can also transmit pressure to the fiber tips for improved coupling of light to the tissue. A connected spectrophotometer (such as a TRS-pulse, PMS, CW, or phased array spectrophotometer) probes deep tissue at large separations of the ports ($\rho$=5 cm to 10 cm) and probes a dermal layer at small separations ($\rho$=0.5 cm to 2 cm).

The hairbrush optical coupler can be used for examination of symmetrical tissue regions of the brain, breast, arm, leg or other, as is described in the WO 92/20273 application. The hairbrush optical coupler can be also employed to detect asymmetrical tissue properties of optically symmetrical body regions. FIG. 7A depicts the hairbrush coupler attached to the head; specifically, to the parietal bones of a newborn which still has the characteristic opening called anterior fontanel. Input ports 73A and 73B of source probes 72A and 72B, respectively, are located on symmetrical locations of the corresponding parietal bones (or the temporal bones, the occipital bone, etc.). Detection ports 75A and 75B are spaced the same distance ($\rho$, usually 3 cm to 8 cm) from the corresponding input ports 73A and 73B. The spectrophotometer introduces radiation of a selected wavelength at each input port and detects radiation at each detection port. The spectrophotometer stores the detected data separately and correlates them together or with a stored data corresponding to the individual brain regions to identify any asymmetry in tissue properties. Alternatively, the spectrophotometer measures a differential signal directly. Normal tissue provides a substantially symmetrical signal. A detected asymmetry may be caused by a tissue disease, such as localized bleeding, an asymmetric stroke volume, or another pathological condition. (For example, see S. P. Gopinath et al., J. Neurosurg., 79, 1993.)

In another embodiment, a multifiber hairbrush probe is used for imaging of the brain. For this purpose, a series of semirigid 1 mm fibers is embedded in a styrofoam or plastic helmet. When the helmet is attached to the head, the input ports of the fibers project through the hair to the surface of the scalp. The patient's head is covered by, for example, 4 rows of 8 fibers extending from the frontal region to the occipital region. A larger number of fibers is used when a higher resolution of the image is needed. Each fiber is coupled at its optical coupling port to an optical sequencer or multiplexer. This way any fiber may be coupled to a light source or a light detector of an optical imager described in PCT/US 93/05868 or PCT/US 95/15694.

Figure 8:
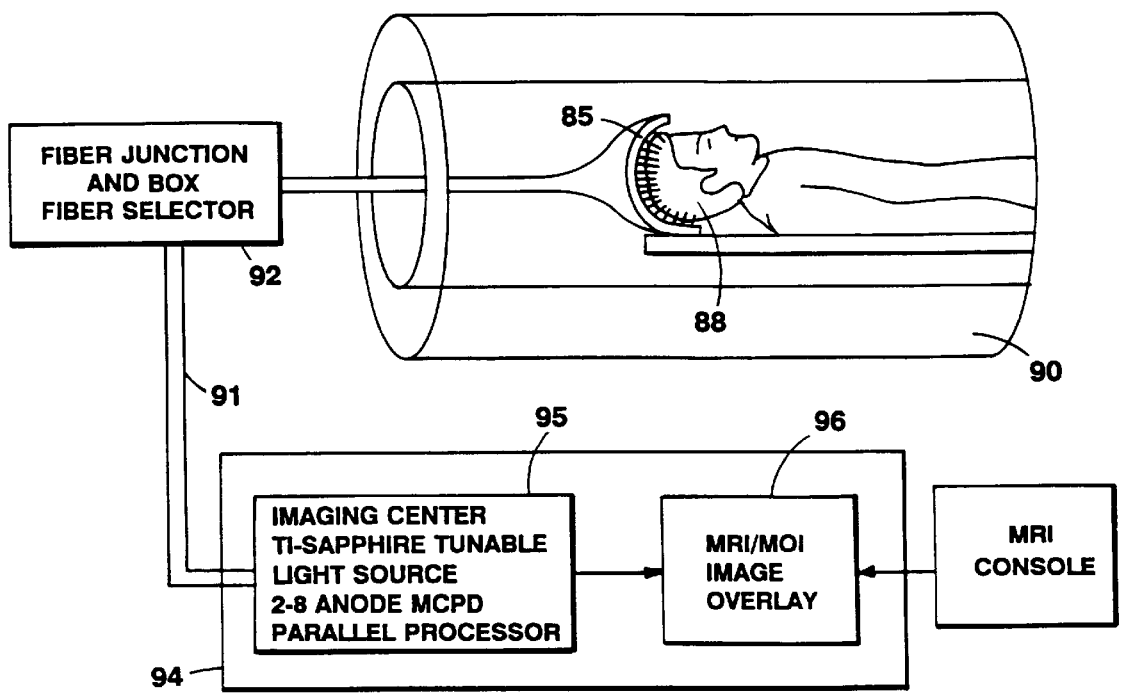
FIGS. 8 and 8A depict a "hairbrush" optical coupling system for optical and MRI examination.

Referring to FIG. 8, in another embodiment, the hairbrush optical coupler is constructed for in vivo examination of tissue using simultaneously magnetic resonance imaging (MRI) and medical optical imaging (MOI). The coupler includes a styrofoam cap 85 with four rows of 8 fibers extending from frontal to occipital region of the patient's head 88 located inside an MRI magnet 90. The optical fibers extend through the hair to the skull and include ferrite caps. Each fiber is coupled at its optical coupling port to a fiber junction box 92. Fiber junction box 92, located outside of magnet 90, has appropriate electromechanical or electro-optical switches to time sequence the switching of a fiber conduit 91 to any one of the 32 fibers coupled to the head 88. The system employs any one or more fibers for transmission and any other fibers for detection. An MRI/MOI control center 94 includes an imaging center 95 and a computer system 96, which is constructed to create and overlay the optical and magnetic images. Coordination of the optical and MRI images is achieved by MRI/optical markers. Three-dimensional markers are formed by coating the fibers with a film exhibiting a magnetically relaxed water-like signal so that each optical fiber appears on an NMR image. This way an optical image generated by the corresponding source and detector fibers is correlated to the MRI image. Importantly, such "labeled" fibers do not interfere with the NMR examination.

Figure 8A:
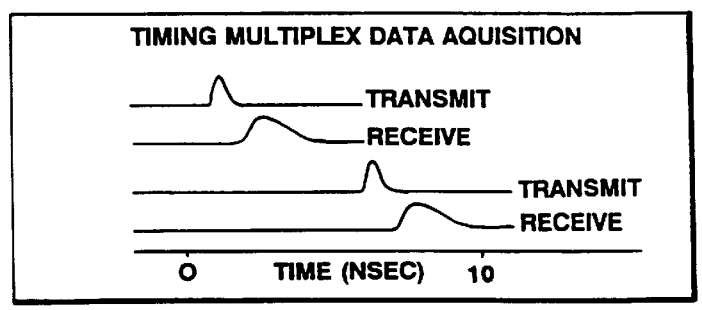

Imaging center 95 employs a TRS system described in U.S. Pat. No. 5,119,815 or in U.S. Pat. No. 5,386,827. The TRS system includes a Ti sapphire tunable laser that generates a series of light pulses of different wavelengths in the NIR region, sensitive to an endogenous or exogenous pigment. The light pulses, generated as shown in a timing diagram of FIG. 8A, are transmitted via fiber conduit 91 to fiber junction box 92. At fiber junction box 92, the signals are multiplexed to the 32 fibers that transmit light to and receive light from appropriate places in the brain. A single optical fiber may also be connected to fiber branches which are attached to various places on the head. The TRS system also includes two 8 multi-anode micro-channel plate detectors. The detector output is send to a parallel computer that generates images congruent with the MRI scan and completed in approximately the same time as the MRI data.

To achieve proper coupling, the fibers are indexed in space to form an array and are encoded appropriately by an index pad that mimics the tissue positions. This identifies the position of the fibers in the array 1 through 32 relative to a master synchronizing pulse. The imaging sequence consists of a series of pulses transmitted through the main fiber to an identified site at selected intervals (e.g., 5 nanosecond). Each pulse generates a photon migration pattern which is received through an identified optical coupling fiber and is recognized by the central computer as originating from a certain receiving fiber or set of receiving fibers by time encoding. The transmitter pulse stimulates all transmit fibers in sequence. Similarly, the pattern received is a composite of all receiver positions. The imaging console "knows" not only the location of the fiber, but also identifies the signal received from the fiber conduit by its time sequence with respect to the synchronizing pulse. The transmission/reception algorithm consists of a sequence of excitation pulses followed by photon diffusion patterns detected at the particular positions selected specifically for the organ being studied.

The system may use a generic transmission/reception algorithm designed for an average organ or a patient specific algorithm. Furthermore, different algorithms may be used for ipsilateral, contralateral, de novo or recurrent brain bleeding. The optical coupler can be attached to the head (or any part of the body) for longer periods of time to monitor evolution of a tissue state (e.g., brain bleeding, compartment syndrome, or changes in a stroke induced volume) during and after administration of a specific drug. For example, the system can also monitor evolution of a stroke induced volume or changes in intracranial pressure after administration of an osmotic agent (e.g., mannitol, glycerol), texamethasone (with its effects delayed for several hours) or another drug that temporarily reduces brain oedema. The system can also monitor evolution of a solute (e.g., glucose) as it equilibrates in the bloodstream.

Computer system 96 provides an overlay of the two images with contrast due to vascularity/vasculogenesis, blood vessels permeability, proliferation/degeneration of intracellular organelles, or some other tissue characteristics. To properly correlate the optical images to the NMR images, the optical images need to have an adequate contrast. The desired gradient of contrast is accomplished by selecting a suitable contrast agent (i.e., an exogenous pigment) and a wavelength of the introduced light. The spectrophotometer may construct separate images based on the scattering coefficient or the absorption coefficient. Furthermore, imaging center 95 may employ an amplitude modulation system or a CW system rather than the TRS system to increase resolution for some types of images.

Figure 9:
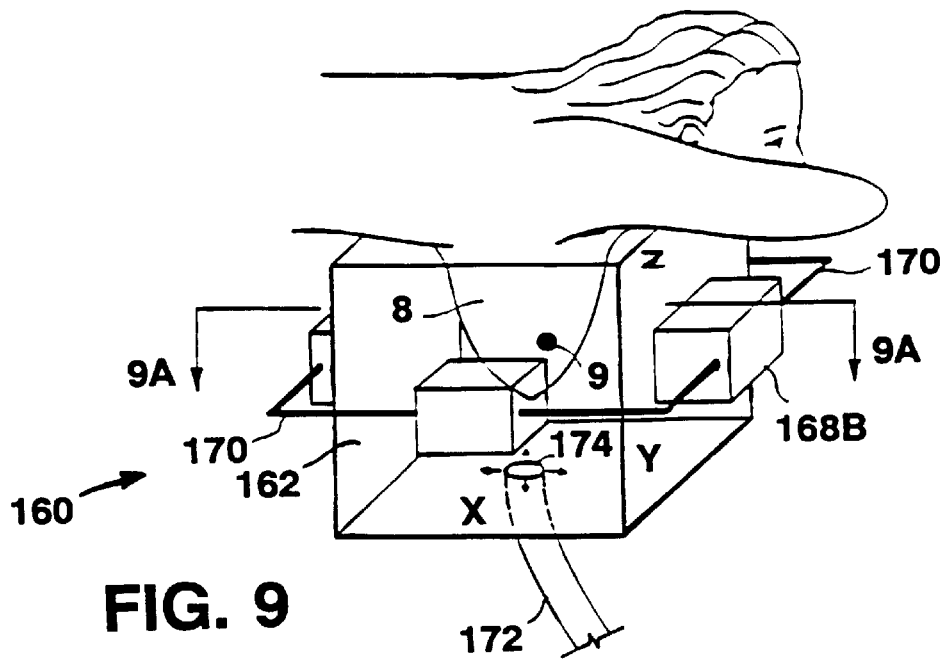
FIGS. 9 and 9A depict a scanning coupling system constructed for examination of breast tissue.
Figure 9A:
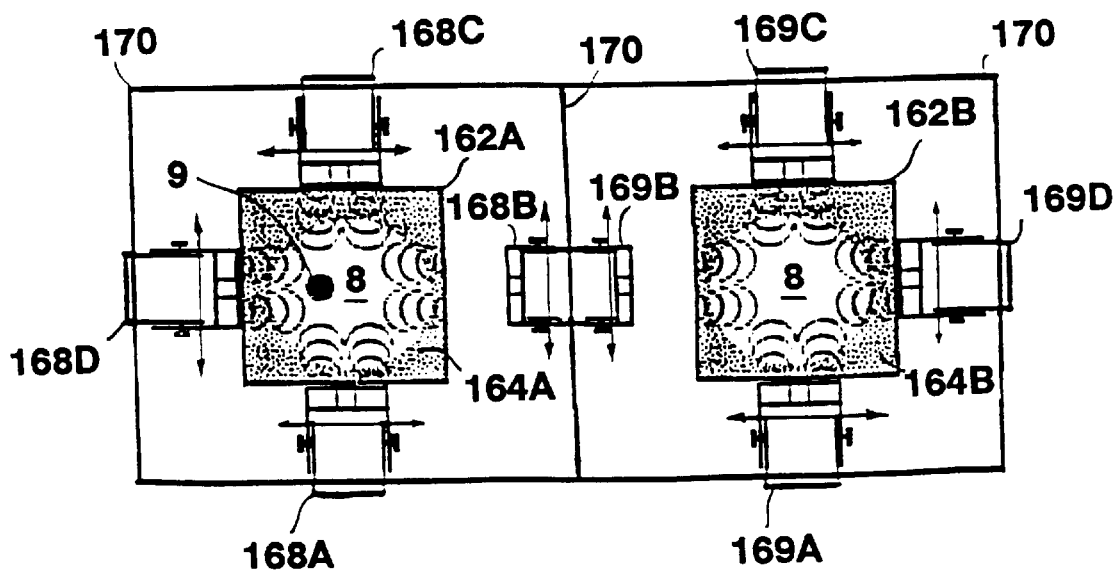

Referring to FIGS. 9 and 9A, another embodiment of the optical coupling system a scanning coupler 160. Scanning coupler 160, constructed for imaging of breast tissue, employs a spectroscopic imaging system described in the WO 93/25145 application or in the PCT/US 95/15694 application. Scanning system 160 includes an optical coupler 162, which may have cubical or cylindrical shape and is filled with optical medium 164. Optical coupler 162 is positioned over the breast near the chest wall. As described above, the optical properties, pressure and volume of medium 164 may be controlled by an external system connected to the coupler by a set of tubes. The optical matching fluid (e.g., twice-diluted J&J baby lotion) is contained within a pliable, optically transparent barrier. The inside walls of coupler 162 may be coated with a film that reflects light in the visible or near infra-red range back to the matching fluid to prevent escape of photons from the tissue surface. The optical coupler may be of different sizes or may have an adjustable volume so that the coupler can have a selected distance between the breast surface and the inside walls. (The preferred distance is about 1 centimeter, but for a very small tissue a larger distance is preferable to achieve semi-infinite boundary conditions.) Thus the coupler is also useful for examination of a small breast or after a surgical removal of the breast tissue. After placement of coupler 162, the volume of medium 164 is adjusted so that the barrier fits snugly around the examined breast. Alternatively, the optical medium is a pliable solid, for example, an absorbing gel containing metallic or oxide spherical particles, silky glass beads as scatterers or a suitable plastic material.

FIG. 9A depicts a set of couplers 162A and 162B for simultaneous scanning of both breasts. Attached to each coupler are source-detector probes (168A, 168B, 168C, 168D, 169A, 169B, 169C, 168D), which include one or more optical sources or detectors described above. The probes are movable on a rail 170. In an automatic positioning system, each probe is connected to a servo motor (step motor) that is operated by a controller. Depending on the spectroscopic system, a fiber 172 (of FIG. 9) may be used to collect, at a detection port 174, radiation that has migrated in the examined tissue and couple the radiation to a detector. Alternatively, fiber 172 may be used to couple, at input port 174, radiation to the examined tissue.

In an electro-optic scan, a computer controller maintains coordinated positions of the probes to the selected combination of the transmitters and receivers. The scan is performed on a single breast or simultaneously on the contralateral breast. The sensitivity of the simultaneous scan is increased by measuring a differential signal. A computer displays the detected signal or the differential signal in a 3 dimensional coordinate system. To increase the resolution, a contrast agent (e.g., cardio-green, indocyanine-green) which is preferentially accumulated in a tumor may by injected intravenously. Several scans are performed to observe the time dependence of the decay and identify a location of a suspected anomaly. The system can also calculate the scattering coefficient and absorption coefficient of the suspected anomaly and the surrounding tissue.

Referring to FIGS. 10 and 10A, in another embodiment, an optical coupler 181 is located at a distal end of a catheter 180. Catheter 180 includes at least two optical conduits 184 and 190, which are at the proximal end connected to a fiber junction box 182 (e.g., a muliplexer, a sequencer). The optical coupler includes at least one input port 186 and at least one detection port 192, separated by a selected distance, and an optical barrier 189 constructed to prevent direct migration of the radiation between the ports. Input port 186 and detection port 192 may also include selected optical medium 188 and 194, respectively. Prior to the spectroscopic examination, optical conduits 184 and 190 may be used for illumination and observation of the internal tissue. At the distal end, catheter 180 may include an inflatable balloon 183. When inflated, balloon 183 presses the optical ports 186 and 192, or pliable optical medium 188 and 194 to the examined tissue.

Alternatively, catheter 180 may include, at its distal end, an optical coupler 200, shown in FIG. 10B, which is constructed and arranged for examination or long term monitoring of brain tissue (or another tissue) of a fetus still located in the uterus. Optical coupler 200 includes a suction ring 202 (or a suction cup) constructed to maintain optical ports 204 and 206 at a selected position, and optical medium 194. Catheter 180 is introduced to the uterus either through the birth canal or through the maternal abdominal wall.

Alternatively, optical coupler 200 designed for visual and spectroscopic examination selected internal tissue, for example, cervix, uterus, gastrointestinal tract, urinary tract, bronchi, and other. Catheter 180 is introduced to the selected tissue region via a body passage or transcutaneously. Optical conduits 184 and 190 are first utilized to locate, visualize and examine the internal tissue by a clinician. If the clinician locates a tissue region that requires further examination, he/she positions the optical input and detection ports for spectroscopic examination utilizing a spectrophotometer optically coupled to the proximal end of catheter 180. The spectroscopic examination is performed by detecting backscattered light that has migrated from the input port to the detection port, or by detecting fluorescent light excited in the examined tissue. Depending on the type of examination, the spectrophotometer is the above-cited CWS, TRS, PMS or phased array spectrophotometer, or a spectrophotometer described in U.S. Pat. Nos. 4,930,516, 5,042,494, 5,106,387, 5,131,398, or 5,261,410.

Catheter 180 may also include a biopsy attachment for taking a biopsy specimen from a tissue region previously examined by the spectrophotometer. The biopsy is performed only if the spectroscopic examination indicates a potentially abnormal tissue. Thus the initial spectroscopic examination eliminates a substantial number of biopsies and saves the related cost.

Figure 11:
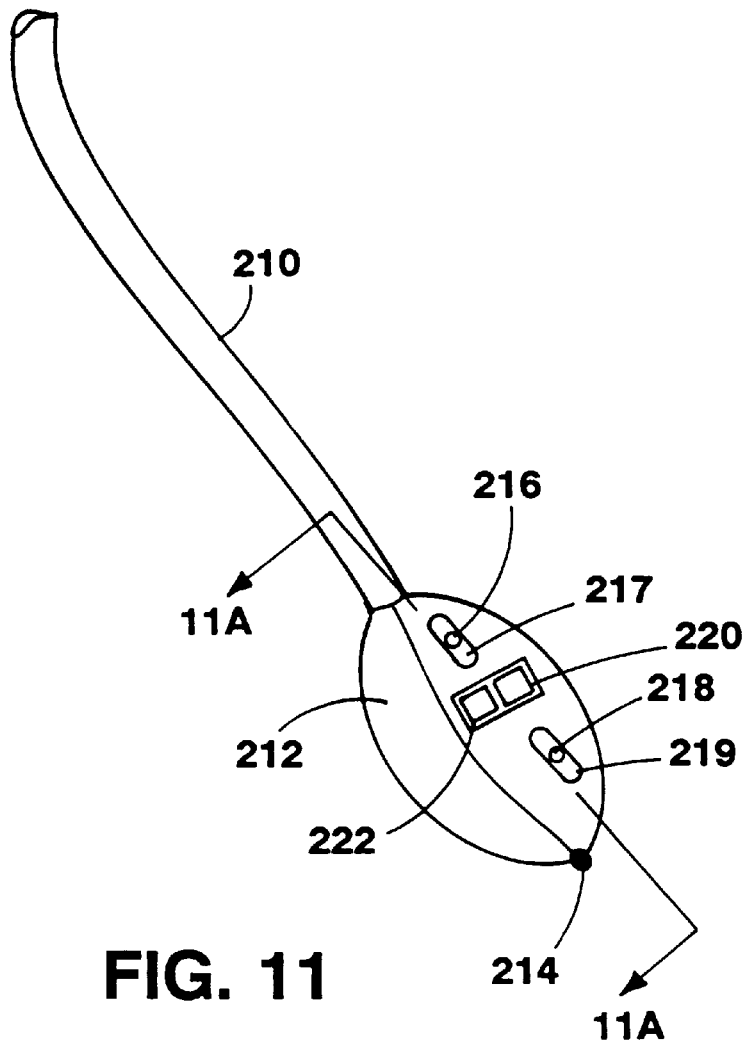
FIGS. 11 and 11A depict a spectrophotometer disposed on a catheter.
Figure 11A:
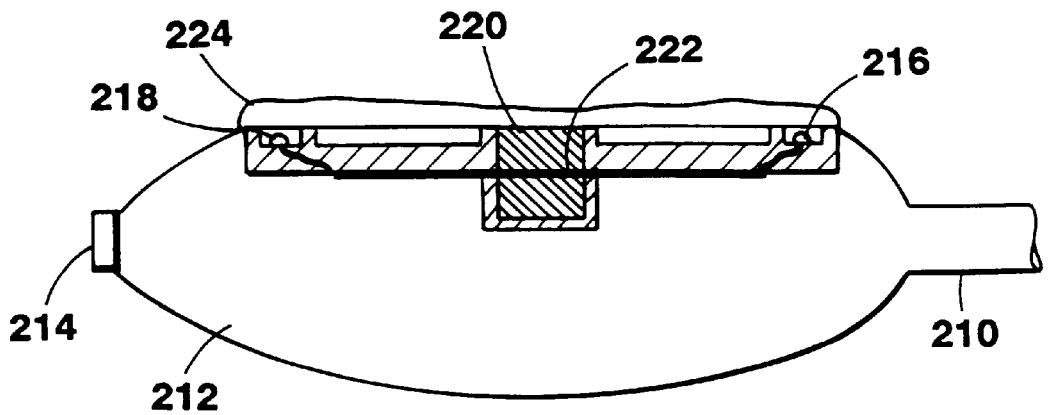

Referring to FIGS. 11 and 11A, in another embodiment, a spectrophotometer is disposed on a catheter 210 (e.g., an endoscopic catheter), which may include an inflatable balloon 212 and endoscope optics 214. The spectrophotometer (e.g., a TRS-pulse, PMS, CW, or phased array spectrophotometer) includes light sources 216 and 218 movable on tracks 217 and 219, respectively, and centrally located detectors 220 and 222. Optical medium 224 is at least partially surrounding the sources and the detectors. In operation, catheter 210, with the balloon deflated, is passed through a body lumen to the position of interest, guided for example, by fluorimetry or by endoscopic viewing. The balloon is then inflated to press optical medium 224 against the tissue of interest. The technique and apparatus may be applied, for example, to body lumens such as the GI tract (e.g., for measurements of GI track wall) or to blood vessels, employing an angiographic catheter for analysis and treatment of occlusions.

A comprehensive system can serve many hospital functions including transduction of vital signals from bedside, from the OR, the ICU, or the ER to a designated computer. The system may include a large number of optrode transducers which may measure all the vital signs (blood pressure, pulse, temperature, respiration) electrocardiogram, electroencephalogram, serum electrolyte levels, and all the features of medical optical imaging (e.g., the simplest detection of hemorrhage, oxygen saturation of hemoglobin, imaging of potential dangers such as stroke, aneurysm rupture, and recurrence of brain bleeding). This information could be carried by single optical fibers with suitable transduction to whatever transmission method is optimal including highly sophisticated PCM.

Other embodiment are within the following claims:

I claim:

1. An optical system for in vivo examination of biological tissue, comprising
    a spectrophotometer constructed and arranged to generate optical radiation of at least one visible or infra-red wavelength and to characterize biological tissue by detecting photons of said wavelength that have migrated in the tissue,
    an array of optical fibers constructed and arranged to transmit said optical radiation between said spectrophotometer and biological tissue,
    said optical fibers including distal ends freely protruding from at least one support in the manner of bristles from a hairbrush and forming an array of optical ports constructed and arranged to couple photons of said radiation to a substantially contiguous tissue region or collect photons of said radiation from a substantially contiguous tissue region, and
    said optical fibers including proximal ends arranged to optically couple said radiation to said spectrophotometer.

2. The optical system of claim 1 wherein said distal ends are sized and distributed to penetrate freely extending hair on the head of a subject to make optical contact directly over an array of points with a surface of the scalp or skin below said hair and near said tissue region.

3. The optical system of claim 2 wherein said array of optical fibers is arranged as an irradiation array with said proximal ends optically coupled to a light source of said spectrophotometer constructed and arranged for brain tissue examination.

4. The optical system of claim 2 wherein said array of optical fibers is arranged as a detection array with said proximal ends optically coupled to a light detector of said spectrophotometer constructed and arranged for brain tissue examination.

5. The optical system of claim 2 further constructed for use in a magnet used for magnetic resonance imaging.

6. The optical system of claim 1 wherein said array of optical fibers is constructed as a handheld probe being sized and configured to be moved and placed against the head.

7. The optical system of claim 1 wherein each said distal end includes an optical matching material constructed and arranged to couple efficiently said radiation between said fiber and the biological tissue region.

8. The optical system of claim 1 wherein said array of optical fibers is arranged as an irradiation array with said proximal ends optically coupled to a light source of said spectrophotometer.

9. The optical system of claim 1 wherein said array of optical fibers is arranged as a detection array with said proximal ends optically coupled to a light detector of said spectrophotometer.

10. The optical system of claim 1 wherein said spectrophotometer is further constructed and arranged for imaging of the brain.

11. The optical system of claim 1 wherein said spectrophotometer is a continuous wave spectrophotometer.

12. The optical system of claim 1 wherein said spectrophotometer is a phase modulation spectrophotometer.

13. The optical system of claim 1 wherein said spectrophotometer is a time resolved spectrophotometer.

14. The optical system of claim 1 wherein said spectrophotometer is a phased array spectrophotometer.

15. An optical system for in vivo examination of biological tissue, comprising:
    a spectrophotometer constructed and arranged to generate optical radiation of at least one visible or infra-red wavelength and characterize biological tissue by detecting photons of said wavelength that have migrated in the tissue,
    a first array of optical fibers including proximal ends optically coupled to a light source of said spectrophotometer, and distal ends freely protruding from a support in the manner of bristles from a hairbrush and forming an array of optical input ports constructed and arranged to introduce said optical radiation into an input region of the biological tissue, and
    a second array of optical fibers including proximal ends optically coupled to provide said radiation to a light detector of said spectrophotometer, and distal ends freely protruding from said support in the manner of bristles from a hairbrush and forming an array of optical detection ports constructed and arranged to collect said optical radiation that has migrated in the biological tissue from said input region to a detection region.

16. The optical system of claim 15 wherein said first and second arrays are constructed to examine a selected tissue volume, said first array being constructed to introduce said radiation into said input region, and said second array being constructed to collect said radiation that has migrated in said volume to said detection region being spaced apart from said input region by a selected distance.

17. The optical system of claim 16 further comprising:
   a third array of optical fibers including proximal ends optically coupled to a light source of said spectrophotometer, and distal ends freely protruding from a second support in the manner of bristles from a hairbrush and forming an array of optical input ports constructed and arranged to introduce said radiation into a second input region, and
   a fourth array of optical fibers including proximal ends optically coupled to provide said radiation to a light detector of said spectrophotometer, and distal ends freely protruding from said second support in the manner of bristles from a hairbrush and forming an array of optical detection ports constructed and arranged to collect said radiation that has migrated in the biological tissue to a second detection region being spaced apart from said second input region by said distance.

18. The optical system of claim 15 wherein said biological tissue is brain tissue.

19. The optical system of claim 18 wherein said distal ends of at least some of said optical fibers are sized and distributed to penetrate freely extending hair on the head of a subject to make optical contact directly over said localized tissue region with a surface of the scalp or skin below said hair.

20. A method of in vivo examination of human tissue comprising:
   providing an array of optical fibers constructed and arranged to transmit optical radiation in a visible to infra-red range between a spectrophotometer and biological tissue, wherein said optical fibers of said array are freely protruding from at least one support in the manner of bristles from a hairbrush;
   generating radiation of said wavelength from a light source of said spectrophotometer,
   introducing said radiation from distal ends of said fibers into an input region of the biological tissue,
   collecting photons that have migrated from said input region to a detection region of the examined tissue,
   detecting said radiation that has migrated in the biological tissue, and
   examining said tissue by processing signals of said detected radiation.

* * * * *